(12) United States Patent
Ren et al.

(10) Patent No.: US 8,278,437 B2
(45) Date of Patent: Oct. 2, 2012

(54) HYDROXYPROPYL-SULFOBUTYL-BETA-CYCLODEXTRIN, THE PREPARATION METHOD, THE ANALYTICAL METHOD, AND THE PHARMACUTICAL APPLICATION THEREOF

(75) Inventors: Yong Ren, Jiangsu (CN); Xueqin Ma, Jiangsu (CN); Shuqin Yu, Jiangsu (CN); Xiaodong Sun, Jiangsu (CN)

(73) Assignee: Hainan Hdeton Science and Technology Co. Ltd. (CN)

( * ) Notice: Subject to any disclaimer, the term of this patent is extended or adjusted under 35 U.S.C. 154(b) by 846 days.

(21) Appl. No.: 12/092,273

(22) PCT Filed: Nov. 28, 2005

(86) PCT No.: PCT/CN2005/002035
§ 371 (c)(1),
(2), (4) Date: Sep. 4, 2008

(87) PCT Pub. No.: WO2007/051358
PCT Pub. Date: May 10, 2007

(65) Prior Publication Data
US 2009/0012042 A1    Jan. 8, 2009

(30) Foreign Application Priority Data

Nov. 2, 2005   (CN) .......................... 2005 1 0095176

(51) Int. Cl.
*C08B 37/16* (2006.01)
(52) U.S. Cl. ...................................................... 536/103
(58) Field of Classification Search .................. None
See application file for complete search history.

(56) References Cited

U.S. PATENT DOCUMENTS

| | | | |
|---|---|---|---|
| 5,134,127 | A | 7/1992 | Stella et al. |
| 6,046,177 | A | 4/2000 | Stella et al. |
| 6,218,375 | B1 | 4/2001 | Raghavan et al. |
| 2002/0150616 | A1 | 10/2002 | Vandecruys |
| 2002/0160982 | A1 | 10/2002 | Jacobs et al. |
| 2004/0053888 | A1 | 3/2004 | Suzuki et al. |
| 2007/0142324 | A1 | 6/2007 | Perly et al. |

FOREIGN PATENT DOCUMENTS

WO        2005042584        5/2005

OTHER PUBLICATIONS

B.W. Mueller and U. Brauns, "Hydroxypropyl-Beta-Cyclodextrin Derivatives: Influence of Average Degree of Substitution on Complexing Ability and Surface Activity", J. Pharm. Sci., 75 (6), pp. 571-572 (1986).
R.A. Rajewski and V.J. Stella, "Applications of Cyclodextrins: 2. In Vivo Drug Delivery", J. Pharm. Sci., 85 (11), pp. 1142-1169 (1996).
M. Bost et al., "The Hemolytic Properties of Chemically Modified Cyclodextrins", Journal of Inclusion Phenomena and Molecular Recognition in Chemistry, 29, pp. 57-63, (1997).
State Drug Administration: Technical requirements of research of new drugs of traditional Chinese medicine, Nov. 12, 1999, abstract only.
Y. Wang et al., "Methods of Determinating the Equilibrium Constants of Cyclodextrin or its Derivatives/Drug Inclusion Complexes and Their Application", [J.] Progress in Pharmaceutical Sciences, 28 (1), pp. 23-28 (2004), abstract only.
R.A. Rajewski et al., "Preliminary Safety Evaluation of Parentally Administered Sulfoalkyl Ether Beta-Cyclodextrin Derivatives", J. Pharm. Sci., 84 (8), pp. 927-932 (1995).
"Solubility Item", People's Republic of China Pharmacopoeia, 2nd edition, 2000, abstract only.
Q. Qu et al., "Sulfoalkyl Ether Beta-Cyclodextrin Derivatives: Synthesis and Characterizations", Journal of Inclusion Phenomena and Macrocyclic Chemistry, 43, pp. 213-221 (2002).
Department of Drug Administration, Ministry of Health: Instructive principle for preclinic study of new Chinese drugs (western drugs), p.42, Jul. 1993, abstract only.
Y. Ren and S. Yu, "The Documents on New Drug Registration, New Pharmaceutic Auxiliary Material: HP4-SBE3-Beta-CD" (2005), abstract only.
S. Xu, "Pharmacological Test Methodology, 2nd version", People Health Press, Beijing, p. 641 (1991), abstract only.
Ren, Yong and Shuqin, Yu; Applicants for New Drug Registration, Pharmaceutical Auxiliary Material: HP567-β-CD, 2005. 13 pages.

*Primary Examiner* — Leigh Maier
(74) *Attorney, Agent, or Firm* — Schmeiser, Olsen & Watts, LLP

(57) ABSTRACT

Hydroxypropyl-sulfobutyl-&bgr;-cyclodextrin, the preparation method, analytical method, and the pharmaceutical application thereof. The hydroxypropyl-sulfobutyl-&bgr;-cyclodextrin which is a derivate of cyclodextrin which is substituted by hydroxypropyl group and sulfobutyl group: n-(2,3,6-O-2-hydroxypropyl)-m-(2,3,6-O-sulfobutyl)-&bgr;-cyclodextrin. The number of substituent groups per mole cyclodextrin is n hydroxypropyl groups and m sulfobutyl groups. "n" represents the average substituent degree of hydroxypropyl groups; "m" represents the average substituent degree of sulfobutyl groups; "n+m=z" is the gross average substituent degree, in which n is a random integer chosen from 1,2,3,4,5,6,7,8,9; m is a random integer chosen from 1,2,3,4,5,6,7,8,9; and the gross average substituent degree z is a random integer chosen from 2,3,4,5,6,7,8,9,10. The present invention shows low haemolysis and low toxicity.

16 Claims, 12 Drawing Sheets

HYDROXYPROPYL-SULFOBUTYL-BETA-CYCLODEXTRIN, THE PREPARATION METHOD, THE ANALYTICAL METHOD, AND THE PHARMACUTICAL APPLICATION THEREOF

FIELD OF THE INVENTION

The present invention relates to a drug carrier—hydroxypropyl-sulfobutyl-β-cyclodextrin, particularly relates to a derivate of cyclodextrin which is substituted by hydroxypropyl group and sulfobutyl group, the preparation method, analytical method, and the pharmaceutical application as a drug carrier thereof.

BACKGROUND OF THE INVENTION

Cyclodextrin (cyclodextrin, CD) is a natural cyclo-oligosaccharides product bonded by glucosidic bond of 6-15 glucose molecules after hydrolysed and bonded by the cyclodextrin gluconotransferase (CGT'ase), the common products are α-, β- and γ-CD, containing 6, 7, 8 glucose molecules respectively, presenting a circular truncated cone, with a hollow hydrophobic intracavity. The hydroxyl groups of the glucose unit are distributed outside the cavity, with hydrophilic property outside the cavity. With the special molecular structure of "hydrophobic inside and hydrophilic outside", CD can form a super-molecule (inclusion complex) with weak reaction between host and guest molecular with a variety of small organic molecules of suitable size, to improve the physical and chemical property of the small organic molecules. Therefore, it has high research and application values for the molecular recognition, mimic enzymes and chiral separation by chromatography, etc, and the applications on the agriculture, medicine, cosmetics and food industry are more promising.

CD has a wide range of applications and research values in pharmacy, but its applications are restricted for its safety and solubility. The commonly-used β-CD, because of its small solubility small (1.85%), strong hemolysis, and strong irritation and obvious renal toxicity of non-intestinal administration of medicines, is unsuitable for non-intestinal administration, while β-CD derivatives (CDD) can overcome its shortcomings. The safety of application in pharmacy for CDD is primary consideration, which promotes the structural transformation of CD to obtain better inclusion complex or carrier materials for drugs.

CD derivative method is to realize by choosing a suitable substituent to substitute the hydroxyl group of the unmodified CD, the inclusion of the substituent destroys the hydrogen bond between the cyclodextrin molecules and changes the solid structure and the property of small inclusion molecules, thus, it changes the physiochemical properties of the water-solubility of the CD, decreases the degree of hemolysis and toxicity and improves the pharmaceutic performance. The type and amount of the substituents introduced (degree of substitution) are of great significance of the property and nature of the derivatives. A "minor" change of the type and degree of substitution generally lead to the significant change of the property and nature of the CD derivatives. A typical example is the impact of propyl group and hydroxypropyl group with C3 structure on the performance of β-CD, although the difference of the structure of substituents is one oxygen atom, however, propyl-β-CD (Pr-β-CD) can not be used for drugs, but hydroxypropyl-β-CD (HP-β-CD) has been widely used as drug excipients and used in the food industry at present due to its good water solubility, small degree of hemolysis and low toxicity. On the other hand, the change of average degree of substitution can also alter the performance and the use of derivatives, such as SBE-β-CD, the degree of hemolysis of such series of products will decrease with the increase of the degree of substitution, for instance, the degree of hemolysis of the 4-substituted derivative (SBE4-β-CD) and the single substituted derivative (SBE1-β-CD) are higher than the 7-substituted derivative, therefore, SBE7-β-CD (Degree of Substitution 6.0-7.1) can be used as drug excipients (U.S. Pat. No. 5,134,127). In addition, the change of the degree of substitution can also alter the inclusion property, for instance, the higher of the average degree of substitution of HP-β-CD, the less of complexing ability (Muller B W, Brauns U. Hydroxypropyl-B-cyclodextrin derivatives: influence of average degree of substitution on complexing ability and surface activity. J Pharm Sci, 1986, 75 (6): 571-572). The most commonly used is HP5-β-CD of the degree of substitution 5.

The structure of β-CD is characterized by two types of hydroxyl groups with total of 21 on the secondary carbon (HO-C2 and HO-C3) and primary carbon (HO-C6). During the course of derivation, the amount of the substituents and the position of substation will greatly alter, with the characteristics of rich structure isomerization. In the actual preparation, it is too difficult to obtain the derivates of single degree of substitution and the single structure. Besides the single-substituted derivatives, the polysubstituted derivatives for the practical application are the mixture of different degree of substitution at different positions, usually average degree of substitution (DS) is used to denote the degree of substitution of CD derivatives. DS refers to the average number of substituents bound with one mol of unmodified CD, for instance, SBE7-β-CD of degree of substitution of 7 means that unmodified β-CD per unit is connected by 7 sulfobutyl groups on average, but actually the compound contains multiple kinds of substituted components from the degree of 1 to 11. FP5-β-CD means the FP5-β-CD with average degree of substitution of 5, but actually containing the components of multiple degrees of substitution of hydroxypropyl group from 1 to 13.

Intermolecular hydrogen bond of β-CD is main reason for the small water solubility and renal toxicity, so the elimination of the adhesive force of the derivatives can form the groups of intermolecular hydrogen bonds. The introduction of groups due to CD derivation include two major types—hydrophobic group and hydrophilic group, which developed the following five types of derivatives: □ the introduction of hydrophobic group, alkyl-substituted CD derivatives, for instance, 2,6-dimethyl-β-CD (DM-β-CD), random methyl-β-cyclodextrin (RM-βCD) and full methylation-β-cyclodextrin, and diethyl-β-cyclodextrin. □ Hydrophilic group, hydroxyl-substituted derivatives, such as hydroxypropyl-β-CD (HP-β-CD) □ Branched-chain CD derivatives such as, glucose-group (G-β-CD), diglucose group (G-β-CD), maltose-group and di-maltose group-cyclodextrin. □ Hydrophilic carboxyl derivatives, such as carboxymethyl CD (CM-β-CD), and so on □ Ionization substituted-group, such as sulfonic-group CD-SBE4-β-CD and SBE7-β-CD, and so on.

Although the introduction of hydrophilic groups and hydrophobic groups can improve the soluable property of β-CD, the safety and irritation of the derivatives of these two types of groups are quite different. The test showed that, the sequence of degree of hemolysis of typical CDD is: β-CD>DM-β-CD>SBE1-β-CD≈HP-β-CD>SBE4-β-CD>SBE7-β-CD (1.

Rajewski, R A; Stella, V J Applications of cyclodextrins: 2. In vivo drug delivery. J. Pharm. Sci. 85 (11), 1142-1169, 1996). At present, the limited researches show that: the primary hydroxyl-substituted (6OH) of β-CD normally can reduce the degree of hemolysis; and the introduction of positive ions usually can decrease the occurrence of hemolysis, and but the negative ion group has less obvious effect on reduction of the hemolytic effect; zwitterion group can normally increase the degree of hemolysis; while the positive ion groups of strong hydrophilic capacity will almost not cause hemolytic effect (M. Bost, V. Laine, F. Piland, A. Gradelle, J. Defeye, B. Perly, J. Inclusion Phenomena and Molecular Recognition in Chemistry 1997, 29, 57).

But the hemolytic tests of SBE-β-CD series of substituents showed that, with the increase of the degree of substitution of sulfobutyl group, the hemolytic performance of SBE-β-CD will significantly reduce (Rajewski, R A; Stella, V J Applications of cyclodextrins: 2. In vivo drug delivery. J. Pharm. Sci. 85 (11), 1142-1169, 1996). U.S. Pat. No. 5,134,127 reported the structure and usage of the sulfobutyl-substituted CD-ioned derivatives SBE-β-CD, the research shows that, the main advantages of SBE7-β-CD: high water solubility (>50 g/100 g H2O); strong complexing ability; no pharmacological activity, no effect on renal function; used for non-oral preparation; low GMP production costs and wide uses. The medicinal product of SBE-β-CD is SBE7-β-CD, with an average degree of substitution of from 6.0 to 7.1, average molecular weight of 2089~2264 g/mol, which has been used for a number of drug preparation products. Another good medicinal CD derivative is hydroxypropyl-β-CD (BP-β-CD), and the degree of substitution marked in European Pharmacopoeia is within the range from 2.8 to 10.5, and the most commonly-used product is HP5-β-CD of degree of substitution of 5. The product of such substitution degree has less hemolytic property, and excellent complexing ability, thus it is widely used.

At present, most of CD derivatives are single-substituted products. In recent years, mixed substituted derivative method is developed. WO 2005042584 reports a new derivative of dual substituted sulfoalkyl-alkyl-CD (SAEx-AEy-CD). In the invention, the hydrophilic group (sulfoalkyl, SAE) and hydrophobic groups (Alkyl, AE) are introduced into CD simultaneously to realize dual poly-substituted derivation, SAEx-AEy-CD can not only improve the water-solubility, enhance the complexing ability, but also obviously reduce the hemolytic property than alkyl-CD, wherein the hemolytic role of ethyl-methyl-butyl-β-CD derivatives is equivalent to SBE4-β-CD, having good application prospect. The basic features of CD, as a drug carrier, are the complexing ability of drug molecules, and its unique function is to differentiate with other types of drug excipients. CD and its derivatives are usually much larger than the drug's molecular weight, and the CD more than the proportion of drug quality is usually used on the actual application, the practice shows that, CD derivatives of too large molecular weight will allow the ratio of excipients in the preparation too high and thus influence the function of CD, and become an important factor for restriction its application. Therefore, the derivation of CD should not only consider the water-solubility and safety, but also should control the molecular weight of the derivatives within a reasonable scope.

SUMMARY OF THE INVENTION

The present invention is to improve the water solubility of the unmodified CD and prepare the safe, effective CD derivatives of appropriate molecular weight. In order to achieve the goal, two kinds of different structures of hydrophilic substituted groups are introduced into the unmodified CD. By the mixed substituted method of two substituents of different proportions, the CD property is improved.

For the present invention, the compound design, synthesis, structure identification, complexing ability test, hemolytic test, test analysis, toxicity test and general pharmacological tests are adopted.

Technical solutions provided by the present invention are:

1) Determination of hydrophilic substituted group and degree of substitution: using hydroxypropyl and sulfobutyl as the substituents, and hemolytic property—degree of substitution relation and hemolytic property—distribution coefficient of molecule (Log P) relation, and considering the molecular weight restriction of the derivatives, design series of HPn-SBEm-β-CD derivatives.

2) Synthesize the design substance by base catalysis continuous reaction method: using unmodified CD as raw material, 1,2-propylene oxide and 1,4-butyl sultone as the reacting reagents to prepare the products by base catalysis in water solution.

3) Identification of the structure of derivatives: effectively differentiate the mono-substituted derivate and its mixture with HPn-SBEm-CD by HPLC and dialysis methods; identify the structure of HPn-SBEm-β-CD by IR, 1HNMR and DSC spectrum, to determine the degree of substitution n and m, and the chromatography is used to analyse the products.

4) Inclusion complex test determination of inclusion complex of HPn-SBEm-β-CD on ionic or non-ionic active molecules; preparation conditions of test inclusion complex; identification of inclusion complex by DSC spectrum.

5) Hemolytic test: conduct hemolytic test with the controls of unmodified CD, HP5-β-CD and SBE7-β-CD.

6) Acute toxicity and general pharmacological tests: using HP-β-CD as control, determine the impact of HPn-SBEm-β-CD toxicity on the cardiovascular system and respiratory system of animals by oral and intravenous administration.

I. Hydrophilic Substituted Group and the Determination of Degree of Substitution 2-HP(HP) and sulfobutyl are hydrophilic groups that can effectively reduce the hemolytic effect of the unmodified CD, and the hemolytic relations between the two substituted derivatives is: β-CD>SBE1-β-CD≈HP-β-CD≧SBE4-β-CD>SBE7-β-CD; using CAChe 6.1.8 Worksystem Pro. Program, simulate and calculate the structural parameters of derivatives of substitution degree of hydroxypropyl and sulfobutyl group of 1-10 (such as: charge, dipole moment, improper torsion, van der Waals, molecular orbital energies, hydrogen bond, torsion stretch, Log P, etc), analyze the relevance with the hemolytic performance, and discover that the distribution coefficient (Log P) is related to the substituent type and degree of substitution, the sequence is: β-CD<SBE1-β-CD<HP3-β-CD<HP5-β-CD≦SBE4-β-CD<SBE7-β-CD, the results are negatively correlated to the hemolytic performance.

To achieve this goal, the derivative hydroxypropyl-sulfobutyl-β-CD (HPn-SBEm-β-CD) mixedly substituted by hydroxypropyl and sulfobutyl group, among them, n refers to the average degree of substitution of hydroxypropyl group, m refers to the average degree of substitution of sulfobutyl group. Log P values of HPn-SBEm-β-CD of n=1-9 and m=1-9 are further calculated, and the data are shown in the following Table 1:

TABLE 1

The relation between Log P values of HPn-SBEm-β-CD and the substituent, degree of substitution

|   | 0       | 1     | 2     | 3     | 4     | 5     | 6     | 7     | 8     | 9     |
|---|---------|-------|-------|-------|-------|-------|-------|-------|-------|-------|
| 0 | −8.52** | −8.27 | −8.02 | −7.77 | −7.52 | −7.28 | −7.03 | −6.78 | −6.53 | −6.28 |
| 1 | −8.16   | −7.92 | −7.67 | −7.42 | −7.17 | −6.92 | −6.67 | −6.43 | −6.18 | −5.93 |
| 2 | −7.81   | −7.56 | −7.31 | −7.07 | −6.82 | −6.57 | −6.32 | −6.07 | −5.83 |       |
| 3 | −7.45   | −7.21 | −6.96 | −6.71 | −6.46 | −6.21 | −5.97 | −5.72 |       |       |
| 4 | −7.10   | −6.86 | −6.61 | −6.36 | −6.11 | −5.86 | −5.62 |       |       |       |
| 5 | −6.74   | −6.50 | −6.25 | −6.00 | −5.75 | −5.51 |       |       |       |       |
| 6 | −6.39   | −6.15 | −5.90 | −5.65 | −5.40 |       |       |       |       |       |
| 7 | −6.04   | −5.79 | −5.54 | −5.31 |       |       |       |       |       |       |
| 8 | −5.69   | −5.44 | −5.19 |       |       |       |       |       |       |       |
| 9 | −5.34   | −5.09 |       |       |       |       |       |       |       |       |

*n = degree of substitution of hydroxypropyl group; m = degree of substitution of sulfobutyl group
**n = m = 0, HP$_n$-SBE$_m$-β-CD = β-CD HPn-SBEm-β-CD series of derivatives of average degree of substitution of n+m=Z≦10 are designed, and the distribution of average molecular weight is from 1353 to 2625.

In other words, in the present invention, a hydroxypropyl-sulfobutyl-β-cyclodextrin, substituted by hydroxypropyl and sulfobutyl groups: n-(2,3,6-O-2-hydroxypropyl)-m-(2,3,6-O-sulfobutyl)-β-CD, said CD derivative has the structure of the following general formula:

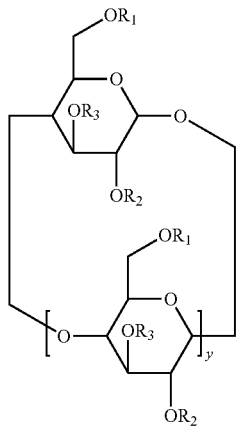

y = 6
$R_1$ = H, $R_2$ = (CH$_2$)$_4$SO$_3$—X, $R_3$ = CH$_2$CH(OH)CH$_3$, or
$R_1$ = H, $R_2$ = CH$_2$CH(OH)CH$_3$, $R_3$ = (CH$_2$)$_4$SO$_3$—X, or
$R_1$ = (CH$_2$)$_4$SO$_3$—X, $R_2$ = H, $R_3$ = CH$_2$CH(OH)CH$_3$, or
$R_1$ = CH$_2$CH(OH)CH$_3$, $R_2$ = H, $R_3$ = (CH$_2$)$_4$SO$_3$—X, or
$R_1$ = (CH$_2$)$_4$SO$_3$—X, $R_2$ = CH$_2$CH(OH)CH$_3$, $R_3$ = H, or
$R_1$ = CH$_2$CH(OH)CH$_3$, $R_2$ = (CH$_2$)$_4$SO$_3$—X, $R_3$ = H, or
$R_1$ = $R_2$ = (CH$_2$)$_4$SO$_3$—X, $R_3$ = CH$_2$CH(OH)CH$_3$, H, or
$R_1$ = $R_3$ = (CH$_2$)$_4$SO$_3$—X, $R_2$ = CH$_2$CH(OH)CH$_3$, H, or
$R_2$ = $R_3$ = (CH$_2$)$_4$SO$_3$—X, $R_1$ = CH$_2$CH(OH)CH$_3$, H, or
$R_1$ = $R_2$ = CH$_2$CH(OH)CH$_3$, $R_3$ = (CH$_2$)$_4$SO$_3$—X, H, or
$R_1$ = $R_3$ = CH$_2$CH(OH)CH$_3$, $R_2$ = (CH$_2$)$_4$SO$_3$—X, H, or
$R_2$ = $R_3$ = CH$_2$CH(OH)CH$_3$, $R_1$ = (CH$_2$)$_4$SO$_3$—X, H, or
$R_1$ = $R_2$ = H, $R_3$ = CH$_2$CH(OH)CH$_3$, (CH$_2$)$_4$SO$_3$—X, or
$R_1$ = $R_3$ = H, $R_2$ = CH$_2$CH(OH)CH$_3$, (CH$_2$)$_4$SO$_3$—X, or
$R_2$ = $R_3$ = H, $R_1$ = CH$_2$CH(OH)CH$_3$, (CH$_2$)$_4$SO$_3$—X
X = Na, K, Li

Preferably, the number of groups substituted by each mol of CD includes: n hydroxypropyl groups and m sulfobutyl groups, wherein, n refers to the average degree of substitution of hydroxypropyl substituents connected to each mol of CD derivatives; m refers to the average degree of substitution of sulfobutyl substituents connected to each mol of CD derivatives; and n+m=Z is the gross average degree of substitution of CD derivative, wherein, in is selected among 1,2,3,4,5,6, 7,8,9; and m is selected among 1,2,3,4,5,6,7,8,9; Z≦10. Wherein said average degree of substitution n and m also include the actual average value ±0.5. In the present invention, the X of hydroxypropyl-sulfobutyl-β-cyclodextrin is recommended Na and/or K derivatives.

II. Preparation of Hydroxypropyl-Sulfobutyl-β-Cyclodextrin

Preferably, the preparation method: using unmodified CD as the raw material, carry out mixed substitution by the reaction steps of continuous feeding without separation of intermediates. Starting materials: β-cyclodextrin; reactive reagents: 1,4-butyl sultone, 1,2-propylene oxide, base catalysis: NaOH, or KOH, or LiOH, preferably NaOH. Reaction system: aqueous solution.

CD is added with 2-4 times of water by mass and 2-17 times of moles of bases, then added with 2-15 times of 1,4-butyl sultone by mol proportion, and 1.5-13 times of 1, 2-propylene oxide by mol proportion. The two reactive reagents are slowing dripped into CD solution, wherein, 2-15 times of bases by mols is required to supplement into the solution that is added with 1,2-propylene oxide, then dripped with the second reagent; wherein, the solution added with 1,4-butyl sultone should react for 5-8 h at the temperature of 80□; and the solution added with 1,2-propylene oxide should react for 5-8 h at room temperature to produce the crude product of hydroxypropyl-sulfobutyl-β-cyclodextrin, neutralized the mixture with hydrochloric acid to pH of 6~7, filtered, then the filtrate is dialyzed, concentrated to obtain the products by pressure reduction. The following process is recommended:

Synthesis Process 1: 2-4 times of water and 3-17 times molar of NaOH are added to the CD, mixed and heated to 80□, slowly dripped into 2-15 times of molar ratio of 1,4-butyl sultone, reacted for 5-8 h, cooled down to the room temperature, then slowly dripped 1.5-13 times of molar ratio of 1,2-propylene oxide, reacted for 7-8 h to produce the crude product of hydroxypropyl-sulfobutyl-β-cyclodextrin, then neutralized to pH 6~7 by hydrochloric acid, filtered, then the filtrate is dialyzed, concentrated to obtain the products by pressure reduction.

Synthesis Process 2: 2-4 times of water and 2 times molar of NaOH are added to the CD, mixed and slowly dripped by 1.5-13 times of molar ratio of 1,2-propylene oxide, reacted for 7-8 hours, then supplemented by 2-15 times of molar ratio of NaOH, heated to 80□, slowly dripped by 2-15 times of molar ratio of 1,4-butyl sulton under constant stirring, reacted for 5-8 h to produce the crude product of hydroxypropyl-sulfobutyl-β-cyclodextrin, then neutralized to pH 6~7 by hydrochloric acid, filtered, then the filtrate is dialyzed, concentrated to obtain the products by pressure reduction.

According to the above said synthetic methods, the product of the required degree of substitution can be obtained by different proportion of feeding. The degree of substitution and physiochemical property of part of products are shown in Table 2-Table 4:

TABLE 2

Average degree of substitution of 11 kinds of hydroxypropyl-sulfobutyl-β-cyclodextrin

| Product | Average molecular weight (g/ml) | Actual average degree of substitution HP | SBE |
|---|---|---|---|
| $HP_1$-$SBE_4$-β-CD | 1756 | 1.2 | 3.5 |
| $HP_2$-$SBE_2$-β-CD | 1620 | 2.1 | 2.3 |
| $HP_2$-$SBE_3$-β-CD | 1713 | 1.8 | 3.0 |
| $HP_3$-$SBE_2$-β-CD | 1616 | 2.7 | 2.1 |
| $HP_3$-$SBE_4$-β-CD | 2000 | 3.2 | 4.3 |
| $HP_3$-$SBE_6$-β-CD | 2171 | 2.6 | 5.6 |
| $HP_4$-$SBE_2$-β-CD | 1676 | 3.9 | 2.0 |
| $HP_4$-$SBE_3$-β-CD | 1799 | 3.8 | 2.8 |
| $HP_5$-$SBE_2$-β-CD | 1677 | 4.6 | 1.8 |
| $HP_5$-$SBE_3$-β-CD | 1923 | 4.9 | 3.2 |
| $HP_6$-$SBE_2$-β-CD | 1720 | 6.0 | 1.5 |

TABLE 3

The physiochemical properties of 11 kinds of hydroxypropyl-sulfobutyl-β-cyclodextrin of different degrees of substitution

| sample | melting point | specific rotation [α] | water content(%) |
|---|---|---|---|
| $HP_1$-$SBE_4$-β-CD | 227~237 | +120.98 | 4.6 |
| $HP_2$-$SBE_2$-β-CD | 245~255 | +171.30 | 5.2 |
| $HP_2$-$SBE_3$-β-CD | 202~212 | +107.97 | 5.0 |
| $HP_3$-$SBE_2$-β-CD | 220~231 | +145.42 | 5.6 |
| $HP_3$-$SBE_4$-β-CD | 227~235 | +116.25 | 4.1 |
| $HP_3$-$SBE_6$-β-CD | 270~280 | +99.06 | 4.2 |
| $HP_4$-$SBE_2$-β-CD | 234~244 | +129.81 | 5.3 |
| $HP_4$-$SBE_3$-β-CD | 232~242 | +115.37 | 4.7 |
| $HP_5$-$SBE_2$-β-CD | 244~255 | +132.68 | 5.3 |
| $HP_5$-$SBE_3$-β-CD | 225~240 | +128.71 | 5.1 |
| $HP_6$-$SBE_2$-β-CD | 236~243 | +149.70 | 5.7 |

TABLE 4

Solvency test of HP2-SBE2-β-CD

| solvent | sample amount (g) | adding quantity of solvent (ml) | solute/solvent | dissolving state | conclusion |
|---|---|---|---|---|---|
| water | 0.5000 | 0.50 | 1/1 | fully dissolved | extremely easily dissolvable |
| 0.1 mol/L HCl | 0.5000 | 0.50 | 1/1 | fully dissolved | extremely easily dissolvable |
| 0.1 mol/LnaOH | 0.5000 | 0.50 | 1/1 | fully dissolved | extremely easily dissolvable |
| Methanol | 0.1000 | 1.00 | 1/10 | fully dissolved | easily dissolvable |
| Ethanol | 0.1000 | 5.00 | 1/50 | dissolved | slightly dissolvable |
| Acetonitrile | 0.1000 | 6.00 | 1/60 | dissolved | slightly dissolvable |
| Hexane | 0.0100 | 100 | 1/10000 | turbidity of solution | non-dissolvable |
| Ethyl acetate | 0.0100 | 100 | 1/10000 | turbidity of solution | non-dissolvable |
| Trichloromethane | 0.0100 | 100 | 1/10000 | turbidity of solution | non-dissolvable |
| Acetone | 0.0100 | 100 | 1/10000 | turbidity of solution | non-dissolvable |
| 50% methanol solution | 0.1000 | 1.00 | 1/10 | dissolved | easily dissolvable |
| 50% ethanol solution | 0.1000 | 2.00 | 1/20 | dissolved | dissolvable |
| 30% acetonitrile solution | 0.1000 | 3.00 | 1/30 | dissolved | dissolvable |

Solubility: based on "Compilation of guidelines of pre-clinical research of new drugs(western medicine)", refer to the test under Solubility Item of "People's Republic of China Pharmacopoeia", $2^{nd}$ edition, 2000.

HPLC and dialysis methods are adopted to differentiate the product and the mixture of hydroxypropyl-β-CD (HP-β-CD), β-CD (β-CD) and sulfobutyl-β-CD.

1. HPLC method: HPLC spectra of HP-β-CD, β-CD, HP2-SBE3-β-CD are shown in FIGS. 1, 2, and 3 respectively. Under the chromatographic conditions, HP-β-CD elution spectrum has a number of broad peak, with the retention time about 3, 10, 13, 16 min; and β-CD has a single broad peak, retention time of about 10 min; while HP2-SBE3-β-CD elution spectrum present a single broad peak, with retention time of 3 min, without HP-β-CD and β-CD characteristic peak, which indicates that hydroxypropyl-sulfobutyl-β-cyclodextrin does not contain HP-β-CD and β-CD. Spectral features combined with 1HNMR spectrum show that: hydroxypropyl-sulfobutyl-β-cyclodextrin is not the physical mixture of β-CD and hydroxypropyl-β-CD and sulfobutyl-β-CD.

2. Dialysis method: Test results show that after dialysis of the mixed samples of HP2-β-CD and SBE6-β-CD by ratio of 1 to 1, the sample weight will reduce half, and the reserved 1 HNMR spectrum only presents SBE4-β-CD characteristic peak, basically no methyl characteristic peak of HP2-β-CD (more than 90 percent losses due to dialysis); HP2-SBE3-β-CD Comparative Test shows that there is basically no changes of 1 HNMR spectrum (dialysis loss rate <7%). The results indicate that the product obtained herein contains hydroxypropyl and sulfobutyl group, and the sample is the product of the mixed substituted by hydroxypropyl-sulfobutyl, rather than the mixture of HP-β-CD and SBE-β-CD.

III. Determination of Purity and Content of Hydroxypropyl-Sulfobutyl-β-CD

1. Determination of Purity of Hydroxypropyl-Sulfobutyl-β-CD

Hydroxypropyl-sulfobutyl-β-CD under the present invention is a series of CD derivatives composed by different degree of substitution of hydroxypropyl group and different degree of substitution of sulfobutyl group. According to the above said preparation method, the main impurities and limited amount required are shown in the following table 5:

TABLE 5

Main impurities of hydroxypropyl-sulfobutyl-β-CD

| Impurities | sources of impurities | limited amount of impurities (%) |
|---|---|---|
| CD | residue | <1.5% |
| γ-hydroxybutyrate sulfonate | residue | <2 ppm |
| 1,2-propanediol | hydrolysis product | <2.5% |

Under the present invention, HPLC method is adopted to analyze and detect the residual CD, and GC method is adopted to analyze and detect γ-hydroxybutyrate sulfonate and 1,2-propylene glycol, which is illustrated by taking HP2-SBE3-β-CD as an example.

Detection of Residues of CD by HPLC Method:

The residual amount of β-CD in HP2-SBE3-β-CD detected by HPLC method is 0.8% (FIG. 4).

Detection of γ-Hydroxybutyrate Sulfonate and 1,2-Propanediol by GC Method:

The contents of γ-hydroxybutyrate sulfonate and 1,2-propylene glycol is 1.2 ppm, 1.0% respectively by GC method (FIG. 5).

2. Determination of Content of Hydroxypropyl-Sulfobutyl-β-CD

Under the present invention, reverse phase-HPLC and external standard method are adopted to determine the content of hydroxypropyl-sulfobutyl-β-CD of different degree of substitution. Taking HP3-SBE6-β-CD as an example, the content of hydroxypropyl-sulfobutyl-β-CD detected by HPLC is 93.7%.

IV. Inclusion of Hydroxypropyl-Sulfobutyl-β-CD and Insoluble Drugs

1. Ion Drugs: Prazosin Hydrochloride

Under the present invention, HP4-SBE2-β-CD was mixed with 1-10 time of water by weight ratio, added with 1/10 of prazosin hydrochloride by weight ratio based on the weight of HP4-SBE2-βCD as 1, fully mixed by stirring for about 2 h; filtered under pressure, then the solid was flushed by water, dried, then the compound containing the inclusion of HP4-SBE2-β-CD and prazosin hydrochloride was obtained.

1) Determination of Inclusion Constant of Prazosin Hydrochloride and Hydroxypropyl-Sulfobutyl-β-Cyclodextrin UV spectrophotometry (Wang Yana, Lu Yapeng, Ren Yong, et, al. Determination and its application of the inclusion constant of cyclodextrin and derivatives/drugs [J]. Pharmacy progress, 2004, 28 (1): 23.) was adopted to measure the inclusion constant Ka of HP2-SBE3-β-CD, HP4-SBE2-β-CD, HP2-SBE2-β-CD, HP3-SBE6-β-CD, HP-β-CD and prazosin hydrochloride respectively, the results are shown in Table 6.

TABLE 6

The inclusion constant of different degrees of hydroxypropyl-sulfobutyl-cyclodextrin and prazosin hydrochloride

| sample | inclusion constant Ka |
|---|---|
| HP-β-CD | 597 |
| HP$_2$-SBE$_3$-β-CD | 610 |
| HP$_4$-SBE$_2$-β-CD | 4131 |
| HP$_2$-SBE$_2$-β-CD | 2697 |
| HP$_3$-SBE$_6$-β-CD | 12048 |

The results show that, hydroxypropyl-sulfobutyl-cyclodextrin has good inclusion ability with prazosin hydrochloride, and the inclusion constant is larger than that of HP-β-CD.

2) Display Thermal Analysis Validation Test of Inclusion Complex

Display thermal analysis of samples are shown in FIG. 6. As shown in the FIG., the physical mixture retains the water peak and melting peak of prazosin hydrochloride, which are basically the simple accumulation of prazosin hydrochloride and HP4-SBE2-β-CD; while in the spectrum of prazosin hydrochloride inclusion of HP4-SBE2-β-CD, the water peak of prazosin hydrochloride disappears, and the position (temperature) and shape (thermal effects) of each peak change, which show that the inclusion complex is formed.

3) Solubilizing Test of Prazosin Hydrochloride

Determination of the solubilization effect of 10% different hydroxypropyl-sulfobutyl-β-CD on prazosin hydrochloride, the results are shown in Table 7.

TABLE 7

The solubilization effect of 10% different hydroxypropyl-sulfobutyl-β-CD on prazosin hydrochloride

| sample | solubility (ug/ml) | multiple of solubilization |
|---|---|---|
| prazosin hydrochloride | 0.0495 | — |
| prazosin hydrochloride/HP$_2$-SBE$_3$-β-CD | 2.0344 | 41.1 |
| prazosin hydrochloride/HP$_3$-SBE$_6$-β-CD | 1.5345 | 31.0 |
| prazosin hydrochloride/HP$_6$-SBE$_2$-β-CD | 3.0200 | 61.0 |
| prazosin hydrochloride/HP$_5$-β-CD | 1.1633 | 23.5 |

The test results show that the hydroxypropyl-sulfobutyl-β-CD has significant solubilization effect on prazosin hydrochloride; the solubilization effect is stronger than that of HP-β-CD.

2. Anionic Drugs: Ibuprofen

HP4-SBE2-β-CD obtained herein was mixed with 1-10 times of water, added with ibuprofen by weight ratio of ¼ based on the weight of HP4-SBE2-β-CD as 1, fully mixed by stirring for about 2 h, filtered by pressure, then the solid substance was flushed with water, dried, and the compound containing the inclusion complex of HP4-SBE2-β-CD and ibuprofen was obtained.

1) Determination of the Inclusion Constant of Ibuprofen and Hydroxypropyl-Sulfobutyl-Cyclodextrin UV spectrophotometry (Wang Yana, Lu Yapeng, Ren Yong, et, al. Determination and its application of the inclusion constant of cyclodextrin and derivatives/drugs [J]. Pharmacy progress, 2004, 28 (1): 23.) was adopted to measure the inclusion constant Ka of HP2-SBE3-β-CD, HP-β-CD and ibuprofen, the results are shown in Table 8.

TABLE 8

The inclusion constant of different degrees of hydroxypropyl-sulfobutyl-cyclodextrin and prazosin hydrochloride

| sample | inclusion constant Ka |
|---|---|
| HP-β-CD | 221 |
| $HP_2$-$SBE_3$-β-CD | 61 |

The above results show that, the inclusion ability of HP2-SBE3-β-CD with ibuprofen is poorer than that of HP-β-CD with ibuprofen, but HP2-SBE3-β-CD still has certain inclusion ability with ibuprofen.

2) Display Thermal Analysis Validation Test of Inclusion Complex

Display thermal analysis of samples are shown in FIG. 7. As shown in the FIG., the physical mixture retains the water peak and melting peak of ibuprofen, which are basically the simple accumulation of ibuprofen and HP4-SBE2-β-CD; while in the spectrum of inclusion complex of ibuprofen and HP4-SBE2-β-CD, the water peak of ibuprofen disappears, and the position (temperature) and shape (thermal effects) of each peak change, which show that the inclusion complex is formed.

3) Solubilizing Test of Ibuprofen

Determination of the solubilization effect of 10% different hydroxypropyl-sulfobutyl-CD on ibuprofen, the results are shown in Table 9.

TABLE 9

The solubilization effect of 10% different hydroxypropyl-sulfobutyl-β-CD on ibuprofen

| sample | solubility (ug/ml) | multiple of solubilization |
|---|---|---|
| ibuprofen | 64.68 | — |
| ibuprofen/$HP_2$-$SBE_3$-β-CD | 330.01 | 5.1 |
| ibuprofen/$HP_3$-$SBE_6$-β-CD | 321.25 | 5.0 |
| ibuprofen/$HP_6$-$SBE_2$-β-CD | 315.03 | 4.9 |

The test results show that the hydroxypropyl-sulfobutyl-β-CD has certain solubilization effect on ibuprofen and the solubilization multiple is about 5.

3. Non-Ionic Drugs: Puerarin

HP4-SBE2-β-CD obtained herein was mixed with 1~10 times of water, added with puerarin by weight ratio of 1/2.7 based on the weight of HP4-SBE2-β-CD as 1, fully mixed by stirring for about 2 h, filtered by pressure, then the solid substance was flushed with water, dried, and the compound containing the inclusion complex of HP4-SBE2-β-CD and puerarin was obtained.

1) Determination of the Inclusion Constant of Puerarin and Hydroxypropyl-Sulfobutyl-β-Cyclodextrin UV spectrophotometry (Wang Yana, Lu Yapeng, Ren Yong, et, al. Determination and its application of the inclusion constant of cyclodextrin and derivatives/drugs [J]. Pharmacy progress, 2004, 28 (1): 23.) was adopted to measure the inclusion constant Ka of HP2-SBE3-β-CD, HP4-SBE2-β-CD, HP2-SBE2-β-CD, HP3-SBE6-β-CD, HP-β-CD and puerarin, the results are shown in Table 10. The results show that, hydroxypropyl-sulfobutyl-cyclodextrin has good inclusion ability with puerarin, and the inclusion constant is larger than that of HP-β-CD.

TABLE 10

The inclusion constant of different degrees of hydroxypropyl-sulfobutyl-cyclodextrin and puerarin

| sample | inclusion constant Ka |
|---|---|
| HP-β-CD | 345 |
| $HP_2$-$SBE_3$-β-CD | 2168 |
| $HP_4$-$SBE_2$-β-CD | 26254 |
| $HP_2$-$SBE_2$-β-CD | 863 |
| $HP_3$-$SBE_6$-β-CD | 1440 |

The above results in Table 10 show that, hydroxypropyl-sulfobutyl-cyclodextrin has good inclusion ability with puerarin, and the inclusion constant is larger than that of HP-β-CD.

2) Display Thermal Analysis Validation Test of Inclusion Complex

Display thermal analysis of samples is shown in FIG. 8. As shown in the FIG., the physical mixture retains the water peak and melting peak of puerarin, which are basically the simple accumulation of puerarin and HP4-SBE2-β-CD; while in the spectra of inclusion complex of puerarin and HP4-SBE2-β-CD, the water peak of puerarin disappears, and the position (temperature) and shape (thermal effect) of each peak change, which show that the inclusion complex is formed.

3) Solubilizing Test of Puerarin

Determination of the solubilization effect of 10% different hydroxypropyl-sulfobutyl-CD on puerarin, the results are shown in Table 11.

TABLE 11

The solubilization effect of 10% different hydroxypropyl-sulfobutyl-CD on puerarin

| sample | solubility (mg/ml) | multiple of solubilization |
|---|---|---|
| puerarin | 5.8 | 1 |
| puerarin/$HP_2$-$SBE_3$-β-CD | 54 | 9.3 |
| puerarin/$HP_3$-$SBE_6$-β-CD | 51.6 | 8.9 |
| puerarin/$HP_6$-$SBE_2$-β-CD | 24.6 | 4.2 |

The test results in Table 11 show that the hydroxypropyl-sulfobutyl-CD has certain solubilization effect on puerarin; the multiple of solubilization effect is about 4-9.

4. Other Drugs

Using HP2-SBE3-β-CD as an example, the inclusion constant and solubilization effect of hydroxypropyl-sulfobutyl-β-CD with other insoluble drugs are investigated, the results are shown in Table 12.

TABLE 12 the inclusion constant and solubilization effect of 10% HP2-SBE3-β-CD with insoluble drugs

| sample | inclusion constant Ka | multiple of solubilization |
|---|---|---|
| Iodoform/HP$_2$-SBE$_3$-β-CD | 2050 | 125 |
| Camptothecin/HP$_2$-SBE$_3$-β-CD | 560 | 35 |
| Lycopene/HP$_2$-SBE$_3$-β-CD | 2566 | 173 |

The results show that the hydroxypropyl-sulfobutyl-β-CD has good solubilization effect on the insoluble drugs.

V. Hemolytic Test of Hydroxypropyl-Sulfobutyl-β-CD (Reference: in Accordance with State Drug Administration the Technical Requirements of Traditional Chinese Medicine Injection, and the Technical Requirements of New Drug Research of Traditional Chinese Medicine, 1999, Nov. 12)

Under the present invention, using β-CD, HP-β-CD, SBE7-β-CD, SBE4-β-CD as controls, the hemolytic test results of 11 kinds of compounds are selected, shown in Table 13 and FIG. 9-FIG. 11. The results showed that: 1) under the condition of test concentration, the degree of hemolysis of all compounds are much less than that of β-CD; 2) the degree of hemolysis of the majority of compounds is less than that of the control products-HP-β-CD and SBE4-β-CD; 3) the degree of hemolysis of compounds HP2-SBE3-β-CD, HP1-SBE4-β-CD, HP3-SBE6-β-CD is less than that of SBE7-β-CD (see FIG. 9), 4) the degree of hemolysis of a small number of compounds is larger than that of HP-β-CD and SBE4-β-CD when the concentration is more than 25 mmol.

The degree of hemolysis of hydroxypropyl-sulfobutyl products under the present invention is directly related to the degree of substitution of hydroxypropyl and sulfobutyl groups: when the degree of substitution of sulfobutyl group is less than or equal to 2, it presents higher degree of hemolysis; and when the degree of substitution of sulfobutyl group is more than or equal to 2.5, the degree of hemolysis significantly reduces; when the gross degree of substitution is 4-7 and the degree of substitution of sulfobutyl group is 3-3.5, the degree of hemolysis is minimum. As long as the average degree of substitution of sulfobutyl group can be controlled 3-6, the products of very low degree of hemolysis can be obtained.

TABLE 13

The results of hemolytic test of all test samples

| sample | concentration without hemolysis (mg/ml) | Concentration when the degree of hemolysis of 50 percent (mg/ml) |
|---|---|---|
| HP$_1$-SBE$_4$-β-CD | 22.83 | 55.33 |
| HP$_2$-SBE$_2$-β-CD | 19.44 | 33.21 |
| HP$_2$-SBE$_3$-β-CD | 20.56 | >60.00 |
| HP$_3$-SBE$_2$-β-CD | 14.54 | 29.89 |
| HP$_3$-SBE$_4$-β-CD | 24.00 | 58.00 |
| HP$_3$-SBE$_6$-β-CD | 34.73 | >76.00 |
| HP$_4$-SBE$_2$-β-CD | 20.11 | 38.54 |
| HP$_4$-SBE$_3$-β-CD | 10.79 | 27.88 |
| HP$_5$-SBE$_2$-β-CD | 10.90 | 28.51 |
| HP$_5$-SBE$_3$-β-CD | 22.11 | 45.19 |
| HP$_6$-SBE$_2$-β-CD | 18.92 | 32.68 |
| SBE$_7$-β-CD | 25.20 | 60.90 |
| SBE$_4$-β-CD | 10.60 | 15.90 |
| HP-β-CD | 8.16 | 12.61 |
| β-CD | 0.28 | 1.14 |

VI. Acute Toxicity Test of Hydroxypropyl-Sulfobutyl-β-Cyclodextrin Drug Carrier (In accordance with State Drug Administration: "Technical requirements of research of new drugs of TCM", 1999, Nov. 12), after investigating the acute toxicity of hydroxypropyl-sulfobutyl=cyclodextrin product, the results showed that, when the mice are administered by intragastric administration of HP4-SBE3-β-CD with dosage of 8000 mg/kg and intravenous injection administration of HP4-SBE3-β-CD with dosage of 2000 mg/kg, no death has been discovered, and no obvious toxic side effects can be observed. The LD50 is not detected and the maximum of tolerance is 8000 mg/kg and 2000 mg/kg respectively, the results indicated that, the toxicity of HP4-SBE3-β-CD is very low. The toxicity data for some injections and excipients are listed on Table 14 for reference.

TABLE 14

Toxicity Indicators of part of injection excipientc

| Sample | Animal to be tested | Administration method | Toxicity LD | dose (mg/kg) |
|---|---|---|---|---|
| HP$_4$-SBE$_3$-β-CD | mouse | Oral | — | 8000 |
| | | intravenous injection | — | 2000 |
| HP$_3$-SBE$_4$-β-CD | mouse | Oral | — | 8000 |
| | | intravenous injection | — | 2000 |
| β-CD | mouse | intraperitoneal injection | LD50 | 788 |
| Propylene glycol | dog | Oral | LD50 | 22 |
| | | intravenous injection | LD50 | 26 |
| 1,3-Butylene glycol | rat | Oral | LD50 | 22.8 |
| | rat | subcutaneous injection | LD50 | 20.06 |
| | | Oral | LD50 | 23.31 |
| | | subcutaneous injection | LD50 | 16.51 |
| amyl alcohol-tert | rat | Oral | LD50 | 1000 |
| | mouse | subcutaneous injection | LD50 | 2100 |
| PEG400 | mouse mouse | intraperitoneal injection | LD50 | 4200 |
| | | subcutaneous injection | LD50 | 10 (ml) |

TABLE 14-continued

Toxicity Indicators of part of injection excipientc

| Sample | Animal to be tested | Administration method | Toxicity LD | dose (mg/kg) |
|---|---|---|---|---|
| Benzyl alcohol | rat | Oral | LD50 | 1230 |
|  | mouse | intravenous injection | LD50 | 64 |
|  |  | Oral | LD50 | 1580 |
|  |  | intravenous injection | LD50 | 480 |
| DMF | mouse | Oral | LD50 | 2800 |
|  |  | subcutaneous injection | LDLo | 1000 |
|  |  | intraperitoneal injection | LD50 | 1400 |
|  |  | intravenous injection | LD50 | 2000 |
| DMA | mouse | Oral | LD50 | 4620 |
|  |  | intraperitoneal | LD50 | 3200 |
|  |  | injection intravenous injection | LD50 | 3020 |
| DMSO | mouse | Oral | LD50 | 16500 |
|  |  | intraperitoneal injection | LD50 | 3000 |
|  |  | subcutaneous | LD50 | 14 |
|  |  | injection intravenous injection | LD50 | 5750 |
| Glyceryl triacetate | mouse mouse | subcutaneous injection | LD50 | 2670 |
|  |  | subcutaneous injection | LD50 | 3250 |
| ethyl lactate | mouse | subcutaneous | LD0 | 2 (ml) |
|  |  | injection | LD50 | 2.5 (ml) |
|  |  |  | LD100 | 3 (ml) |
|  |  | intravenous injection | LD0 | 0.2 (ml) |
|  |  |  | LD50 | 0.6 (ml) |
|  |  |  | LD100 | 1 (ml) |
| Benzyl benzoate | rat | Oral | LD50 | 1700 |
|  | mouse | cutaneous absorption | LD50 | 4000 |
|  |  | Oral | LD50 | 1400 |
| Mannitol | rat | Oral | LD50 | 17 |
|  | mouse | Oral | LD50 | 22 |
|  |  | intraperitoneal | LD50 | 14 |
|  |  | injection intravenous injection | LD50 | 17 |
| Citric acid | mouse | Oral | LD50 | 5040 |
|  |  | intraperitoneal injection | LD50 | 961 |
|  |  | subcutaneous | LD50 | 2700 |
|  |  | injection intravenous injection | LD50 | 42 |
| Sodium deoxycholate | mouse | intraperitoneal injection | LD50 | 1400 |
|  |  | subcutaneous | LD50 | 75 |
|  |  | injection Oral | LD50 | 815 |

Bibliography:
□Hou Huimin Wanghao Zhang Guangjie: Medicinally Auxiliary Material and Application Technology, the $2^{nd}$ Edition [M]
□Rajewski R. A.; Traiger, G.; Bresnahan, J.; Jaberaboansari, P.; Stella, V. J.; Thompson, D. O.; Preliminary Safety Evaluation of Parenterally Administered Sulfoalkyl Ether β-Cyclodextrin Derivatives, J. Pharm. Sci. 84(8), 927-932, 1995

VII. General Pharmacological Test of Hydroxypropyl-Sulfobutylether-β-Cyclodextrin (I) Effects on Mouse's Nervous System (Bibliography: 1. Xu, Shuyun Pharmacological Test Methodology, 2nd version, P.641, People Health Press, Beijing, 1991. 2. Medicine Secretary for the Ministry of Health, Guidelines on Preclinical Study of New Pharmaceuticals (weaten drugs), P. 42, July, 1993.)

1. Effect on mouse's ordinary behaviors: the results showed that there was no obvious abnormality of mice's activity, feeding, urine and stools, furs and other indices after administration. Compared with the control group, it showed that there was no obvious effect on mouse's ordinary behaviors.

2. Effect on mouse's spontaneity times: (see Table 15). The results showed that there was no obvious effect on mouse spontaneous activities when HP4-SBE3-β-CD dose administrated was 80 mg/kg, 160 mg/kg and 320 mg/kg. Compared with the control group at different time after administration, the result showed that there was no significant difference and no obvious effect on mouse's spontaneous activities.

TABLE 15

Effect on mouse's spontaneous activities

| Group | Dose mg/kg | Animal quantity n | The frequency of spontaneous activities (times/5 min) at different time (min) after administration | | | | |
|---|---|---|---|---|---|---|---|
| | | | 0 | 30 | 60 | 120 | 180 |
| Blank control | — | 10 | 316 ± 46 | 277 ± 46 | 225 ± 55 | 187 ± 24 | 170 ± 36 |
| $HP_4$-$SBE_3$-β-CD | 80 | 10 | 319 ± 50 | 246 ± 79 | 225 ± 38 | 179 ± 20 | 166 ± 45 |
| $HP_4$-$SBE_3$-β-CD | 160 | 10 | 289 ± 43 | 227 ± 70 | 207 ± 63 | 181 ± 40 | 150 ± 48 |
| $HP_4$-$SBE_3$-β-CD | 320 | 10 | 296 ± 43 | 248 ± 59 | 206 ± 56 | 193 ± 41 | 146 ± 53 |
| chloropromazine | 2 | 10 | 302 ± 75 | 57 ± 40* | 16 ± 20* | 22 ± 19* | 25 ± 28* | x ± sd, Student t test,
*P < 0.05, compared with the control group.

3. Effect on balance test: the result showed that the drop rate of each group is 0 after administration at each time, which indicated there was no obvious effect on balance movement.

The above results showed that HP4-SBE3-β-CD would not change mouse's ordinary behaviors, activity times and balance movement when the intragastric administration doses provided was 80 mg/kg, 160 mg/kg and 320 mg/kg, which indicated that the medicine had no effect on nervous system.

(II) Effect on Anesthetics Dog's Respiratory System and Cardiovascular System (Bibliography: Department of Medical Administration, the Ministry of Health, The Guideline for New Medicine (Western Medicine) Preclinical Study Assembly, P. 42, July, 1993.)

1. Effect on respiratory system test: (The test results are shown in Table 16). The results showed that there was no obvious changes of respiratory frequency or respiratory amplitude of anesthetic dogs within each observation time between the groups administered with various doses of HP4-SBE3-β-CD through duodenum and the control group of normal saline solution; of which, there was no great significance for the groups of various doses of administration after administration for 30, 60, 120, and 180 min compared with no administration of medicines, P>0.05, while, comparing with the control groups, P>0.05, which indicated that, HP4-SBE3-β-CD had no obvious effect on respiratory system of anesthetics dog.

2. Effect on cardiac rate: (The test results see Table 17). The results showed that there was no obvious effect on cardiac rate at various time phases after each dose groups of HP4-SBE3-β-CD was administrated through duodenum. Compared with the groups before administration of medicines and the control group, there were no significant effect (P>0.05), which indicated that the medicine had no obvious effect on cardiac rate of anesthetics dogs.

3. Effect on blood pressure (BP): (The test results see table 18). The result showed that there was no obvious effect on SAP, DAP and MAP of anesthetics dog at various time after HP4-SBE3-β-CD was administrated through duodenum when the dose was 40 mg/kg, 80 mg/kg and 160 mg/kg. Compared with group of dogs before administration of medicines, there was no significant difference (P>0.05), which indicated that the medicine had no obvious effect on blood pressure of anesthetics dogs.

4. Effect on electrocardiogram: (The test results see table 19). The results showed that there was no obvious effect on transmit time of anesthetic ECG wave and voltage amplitude after administration of HP4-SBE3-β-CD through duodenum when doses were 40 mg/kg, 80 mg/kg and 160 mg/kg, and there was no occurrence of arrhythmia. Compared with the control group, there was no significant difference (P>0.05), which indicated that the medicine had no obvious effect on ECG of anesthetics dogs.

Summing up the above results, after administration of HP4-SBE3-β-CD through duodenum when the dose was 40 mg/kg, 80 mg/kg and 160 mg/kg, there are no obvious change on blood pressure, respiration, cardiac rate and ECG of anesthetic dogs, which shows that HP4-SBE 3-β-CD has no obvious effect on respiration system and cardiac system of anesthetic dogs, while after administration of HP-β-CD, for instance, 10-100.0 mg/kg, there were no obvious effect on respiratory amplitude, respiratory frequency, blood pressure and ECG; when the doses were 40 mg/kg, 120 mg/kg and 400 mg/kg, there was no obvious effect on mouse fasting blood glucose, however, there is slight reduction of impellent function of mouse stomach intestine when the doses were 120 mg/kg and 400 mg/kg. (Yong Ren and Shuqin Yu, the Documents on New drug Registration, New Pharmaceutic Auxiliary Material: HP567-β-CD, 2005)

TABLE 16

$HP_4$-$SBE_3$-β-CD's effect on respiration of anesthetic dog

| Index | | Dose (mg/kg) | Time after administration (min) | | | | | | |
|---|---|---|---|---|---|---|---|---|---|
| | | | 0 | 5 | 10 | 30 | 60 | 120 | 180 |
| respiratory frequency (time/min) | Control group | — | 17.8 ± 5.60 | 17.0 ± 6.96 | 17.3 ± 6.92 | 16.7 ± 6.09 | 18.3 ± 5.85 | 19.5 ± 5.92 | 20.0 ± 5.25 |
| | $HP_4$-$SBE_3$-β-CD | 40 | 19.5 ± 3.67 | 20.8 ± 5.15 | 20.5 ± 5.09 | 20.5 ± 5.17 | 20.7 ± 3.72 | 19.3 ± 4.23 | 20.0 ± 5.25 |
| | | 80 | 18.5 ± 6.41 | 19.2 ± 6.70 | 19.7 ± 5.89 | 20.3 ± 5.50 | 19.7 ± 6.05 | 19.8 ± 6.99 | 21.3 ± 7.94 |
| | | 160 | 18.0 ± 4.24 | 18.8 ± 4.45* | 19.0 ± 3.16 | 19.0 ± 3.46 | 19.7 ± 2.73 | 20.8 ± 3.81 | 20.3 ± 2.94 |
| respiratory amplitude (mm) | Control group | — | 14.2 ± 1.33 | 14.7 ± 1.86 | 14.7 ± 1.63 | 14.8 ± 0.76 | 13.5 ± 0.84 | 13.2 ± 1.47 | 14.0 ± 1.09 |
| | $HP_4$-$SBE_3$-β-CD | 40 | 13.3 ± 1.50 | 13.5 ± 1.87 | 13.3 ± 1.97 | 14.8 ± 1.83 | 14.8 ± 2.04 | 14.3 ± 1.21 | 14.7 ± 2.06 |
| | | 80 | 13.5 ± 1.76 | 14.3 ± 0.82 | 15.2 ± 1.72 | 14.5 ± 1.76 | 14.3 ± 1.86 | 14.8 ± 1.16 | 15.0 ± 1.90 |
| | | 160 | 13.5 ± 2.73 | 14.0 ± 2.83 | 13.5 ± 2.81 | 14.2 ± 2.32 | 13.8 ± 1.94 | 14.0 ± 1.90 | 14.2 ± 2.14 |

X ± S; n = 6, student t test, compared with the control group, P > 0.05.

TABLE 17

$HP_4$-$SBE_3$-$\beta$-CD's effect on cardiac rate of anesthetic dog

| Group | Dose (mg/kg) | cardiac rate of tested animal (times/min) at different time after administration (min) | | | | | | |
|---|---|---|---|---|---|---|---|---|
| | | 0 | 5 | 10 | 30 | 60 | 120 | 180 |
| Control group | — | 187.3 ± 10.6 | 189.2 ± 14.4 | 189.6 ± 25.7 | 185.7 ± 14.9 | 191.3 ± 20.2 | 192.7 ± 18.2 | 190.0 ± 18.8 |
| $HP_4$-$SBE_3$-$\beta$-CD | 40 | 188.8 ± 18.2 | 187.5 ± 16.0 | 188.2 ± 21.0 | 188.2 ± 19.2 | 189.3 ± 22.6 | 188.5 ± 23.2 | 190.0 ± 19.1 |
| | 80 | 187.5 ± 18.5 | 193.2 ± 16.5 | 192.3 ± 16.5 | 194.5 ± 18.9 | 198.3 ± 18.9 | 195.8 ± 18.8 | 197.8 ± 18.7 |
| | 160 | 185.3 ± 22.1 | 187.8 ± 20.9 | 184.8 ± 20.8 | 187.3 ± 23.8 | 188.5 ± 21.4 | 190.7 ± 19.2 | 188.8 ± 18.0 |

X ± S; n = 6, student t test, compared with the control group, P > 0.05.

TABLE 18

$HP_4$-$SBE_3$-$\beta$-CD's effect on blood pressure of anesthetics dog

| Index | group | dose (mg/kg) | Bl Blood pressure of tested animal (mmHg) at different time after administration (min) | | | | | | |
|---|---|---|---|---|---|---|---|---|---|
| | | | 0 | 5 | 10 | 30 | 60 | 120 | 180 |
| SAP | Control group | — | 145.5 ± 15.6 | 147.2 ± 17.3 | 145.3 ± 15.6 | 144.0 ± 13.8 | 144.7 ± 18.2 | 144.0 ± 19.2 | 144.0 ± 18.3 |
| | $HP_4$-$SBE_3$-$\beta$-CD | 40 | 148.3 ± 15.0 | 145.0 ± 16.0 | 144.8 ± 17.3 | 147.5 ± 15.8 | 145.8 ± 16.3 | 147.2 ± 18.6 | 147.7 ± 20.2 |
| | | 80 | 144.7 ± 15.5 | 144.5 ± 14.8 | 144.7 ± 15.7 | 148.0 ± 15.5 | 150.3 ± 15.9 | 149.7 ± 14.9 | 148.7 ± 13.4 |
| | | 160 | 146.0 ± 14.8 | 145.3 ± 16.6 | 143.5 ± 17.0 | 144.3 ± 17.2 | 148.0 ± 13.3 | 149.5 ± 13.2 | 149.3 ± 12.8 |
| DAP | Control group | — | 104.8 ± 10.6 | 104.7 ± 10.6 | 103.3 ± 11.0 | 102.5 ± 11.7 | 103.7 ± 13.0 | 101.8 ± 14.4 | 102.5 ± 14.1 |
| | $HP_4$-$SBE_3$-$\beta$-CD | 40 | 104.0 ± 9.4 | 104.0 ± 11.3 | 104.3 ± 10.4 | 103.3 ± 11.1 | 101.8 ± 12.7 | 101.8 ± 11.8 | 100.2 ± 15.1 |
| | | 80 | 103.0 ± 10.6 | 103.2 ± 10.1 | 102.8 ± 9.7 | 103.3 ± 10.6 | 105.5 ± 12.2 | 104.7 ± 9.4 | 104.7 ± 10.2 |
| | | 160 | 101.5 ± 9.3 | 99.5 ± 10.9 | 98.7 ± 10.0 | 99.3 ± 11.7 | 100.0 ± 9.0 | 103.7 ± 9.8 | 102.3 ± 10.4 |
| MAP | Control group | — | 121.3 ± 12.7 | 120.7 ± 12.8 | 120.8 ± 12.4 | 117.8 ± 11.3 | 119.5 ± 16.4 | 118.2 ± 17.4 | 119.2 ± 17.2 |
| | $HP_4$-$SBE_3$-$\beta$-CD | 40 | 120.5 ± 11.5 | 118.8 ± 12.5 | 118.3 ± 11.8 | 120.3 ± 12.6 | 119.0 ± 14.1 | 119.2 ± 15.0 | 115.3 ± 14.5 |
| | | 80 | 119.2 ± 11.2 | 119.7 ± 11.4 | 119.2 ± 11.4 | 120.5 ± 12.7 | 122.2 ± 13.6 | 120.7 ± 12.3 | 121.3 ± 11.4 |
| | | 160 | 119.0 ± 11.8 | 117.8 ± 13.1 | 116.0 ± 13.2 | 116.2 ± 12.8 | 117.8 ± 11.1 | 119.2 ± 11.3 | 119.7 ± 11.4 |

X ± S; n = 6, student t test, compared with the control group, P > 0.05, compared with the group without administration of medicine, P > 0.05

TABLE 19

$HP_4$-$SBE_3$-$\beta$-CD's effect on electrocardiogram of anesthetic dog

| Index | Group | Dose (mg/kg) | Time after administration (min) | | | | | | |
|---|---|---|---|---|---|---|---|---|---|
| | | | 0 | 5 | 10 | 30 | 60 | 120 | 180 |
| P-R (s) | Control group | — | 0.105 ± 0.01 | 0.105 ± 0.01 | 0.105 ± 0.01 | 0.105 ± 0.01 | 0.105 ± 0.01 | 0.105 ± 0.01 | 0.105 ± 0.01 |
| | $HP_4$-$SBE_3$-$\beta$-CD | 40 | 0.105 ± 0.01 | 0.105 ± 0.01 | 0.105 ± 0.01 | 0.105 ± 0.01 | 0.105 ± 0.01 | 0.105 ± 0.01 | 0.105 ± 0.01 |
| | | 80 | 0.102 ± 0.007 | 0.102 ± 0.007 | 0.102 ± 0.007 | 0.102 ± 0.007 | 0.102 ± 0.007 | 0.102 ± 0.007 | 0.102 ± 0.007 |
| | | 160 | 0.104 ± 0.008 | 0.104 ± 0.008 | 0.104 ± 0.008 | 0.104 ± 0.008 | 0.104 ± 0.008 | 0.104 ± 0.008 | 0.104 ± 0.008 |
| QRS (s)P | Control group | — | 0.044 ± 0.003 | 0.044 ± 0.003 | 0.044 ± 0.003 | 0.044 ± 0.003 | 0.044 ± 0.003 | 0.044 ± 0.003 | 0.044 ± 0.003 |
| | $HP_4$-$SBE_3$-$\beta$-CD | 40 | 0.044 ± 0.003 | 0.044 ± 0.003 | 0.044 ± 0.003 | 0.044 ± 0.003 | 0.044 ± 0.003 | 0.044 ± 0.003 | 0.044 ± 0.003 |
| | | 80 | 0.044 ± 0.003 | 0.044 ± 0.003 | 0.044 ± 0.003 | 0.044 ± 0.003 | 0.044 ± 0.003 | 0.044 ± 0.003 | 0.044 ± 0.003 |
| | | 160 | 0.045 ± 0.003 | 0.045 ± 0.003 | 0.045 ± 0.003 | 0.045 ± 0.003 | 0.045 ± 0.003 | 0.045 ± 0.003 | 0.045 ± 0.003 |
| Q-T (s) | Control group | — | 0.206 ± 0.017 | 0.206 ± 0.017 | 0.206 ± 0.017 | 0.206 ± 0.017 | 0.206 ± 0.017 | 0.206 ± 0.017 | 0.206 ± 0.017 |
| | $HP_4$-$SBE_3$-$\beta$-CD | 40 | 0.210 ± 0.019 | 0.211 ± 0.019 | 0.210 ± 0.019 | 0.211 ± 0.019 | 0.210 ± 0.019 | 0.210 ± 0.019 | 0.211 ± 0.019 |
| | | 80 | 0.208 ± 0.012 | 0.208 ± 0.012 | 0.208 ± 0.012 | 0.205 ± 0.016 | 0.206 ± 0.015 | 0.207 ± 0.013 | 0.207 ± 0.013 |
| | | 160 | 0.208 ± 0.016 | 0.206 ± 0.018 | 0.208 ± 0.016 | 0.207 ± 0.017 | 0.207 ± 0.017 | 0.208 ± 0.016 | 0.208 ± 0.016 |

X ± S; n = 6, student t test, compared with the control group, P > 0.05, compared with the group without administration of medicine, P > 0.05.

ADVANTAGES OF THE INVENTION

1. Hydroxypropyl-sulfobutyl-β-cyclodextrin synthesized in the present invention has small hemolysis and low toxicity. The hemolysis of various substituents with the scope is lower than that of β-cyclodextrin and is also lower than the common pharmaceutical excipient—hydroxypropyl-β-cyclodextrin, and hemolysis of part of substituents is lower than the pharmaceutical excipient-sulfobutyl-β-cyclodextrin The hemolysis of hydroxypropyl-sulfobutyl-β-cyclodextrin is related to the substitution degree of hydroxypropyl and sulfobutyl and has a minimum scope of hemolysis substitution degree: the products of hydroxypropyl substitution degree n within the range of 2.0-5.0 show lower hemolysis, and the products of sulfobutyl substitution degree m within the range of 3.0-4.5 show very low hemolysis. When the hydroxypropyl substitution degree n>6, the hemolysis is increased; sulfobutyl substitution degree m≦2.0, a relatively larger hemolysis presents; when sulfobutyl substitution degree m>2.5, the hemolysis is significantly reduced, summing up the results, when the gross degree of substitution is within 4-7, derivatives of low hemolysis can be obtained, such as HP2-SBE3-β-CD, HP3-SBE2-β-CD, HP1-SBE4-β-CD and HP4-SBE2-β-CD, etc, and the Log P values of the derivatives of such degrees of substitution is within the range of −6.80-−7.10.

The hemolysis of derivatives of ethyl-sulfobutyl-β-cyclodextrin, propyl-sulfobutyl-β-cyclodextrin reported in WO 2005042584 is equivalent to that of SBE4.6-β-CD.

2. The hydroxypropyl-sulfobutyl-β-cyclodextrin obtained herein has good solubility and its water solubility is more than or equal to 50%, which also have better solubility in organic solvent (as shown in Table 4). The good solubility is very beneficial to inclusion of insoluble drugs to facilitate simplification of the inclusion process and the analysis and detection of hydroxypropyl-sulfobutyl-β-cyclodextrin products, as well as control on the product quality.

3. The hydroxypropyl-sulfobutyl-β-cyclodextrin obtained herein has stronger inclusion ability, especially for the inclusion of cation and neutral ion drugs and also has certain inclusion ability of the anion drugs. After inclusion of drugs, the solubility of the drugs is improved, particularly important to improve the bioavailability of insoluble drugs.

4. Hydroxypropyl-sulfobutyl-β-cyclodextrin prepared herein has an appropriate average molecular weight, for instance, the HP1-SBE4-βCD, HP2-SBE3-β-CD and HP3-SBE2-β-CD of gross degree of substitution of 5, whose average molecular weight is within the range 1571-1730 (equivalent to the molecular weight of HP7-β-CD), is far below the average molecular weight within 2089-2264 of SBE7-β-CD. The inclusion quantity per unit weight of the drug obtained herein is higher than that of SBE7-β-CD, which means that for the same weight of inclusion materials, the product obtained herein will include 31%-33% more drugs than that of SBE7-β-CD, which has important and realistic significance to control the amount of excipients used, and thus greatly improve the application feasibility of the product obtained herein.

5. The preparation method of the present invention is simple with high yield and stable quality. The yield of weight of series of hydroxypropyl-sulfobutyl-β-Cyclodextrin is more than or equal to 110. In addition, the raw materials for the present invention preparation method is easy to be available (β-CD, 1,2-propylene oxide, 1,4-butane sultone sold in the market), and the production cost is low. Necessary sulfobutyl-β-Cyclodextrin with a degree of substitution product can be obtained in the preparation process through regulating the feeding ratio. The chromatography method has high sensitivity, strong selectivity and simple operation for product analysis.

6. The product obtained herein has stable nature, non-toxicity, non-inflammability, non-explosibility, no environmental pollution, non-perishable, easy for storage and transportation.

DETAILED DESCRIPTION OF THE INVENTION

EXAMPLE 1

Figure 1:
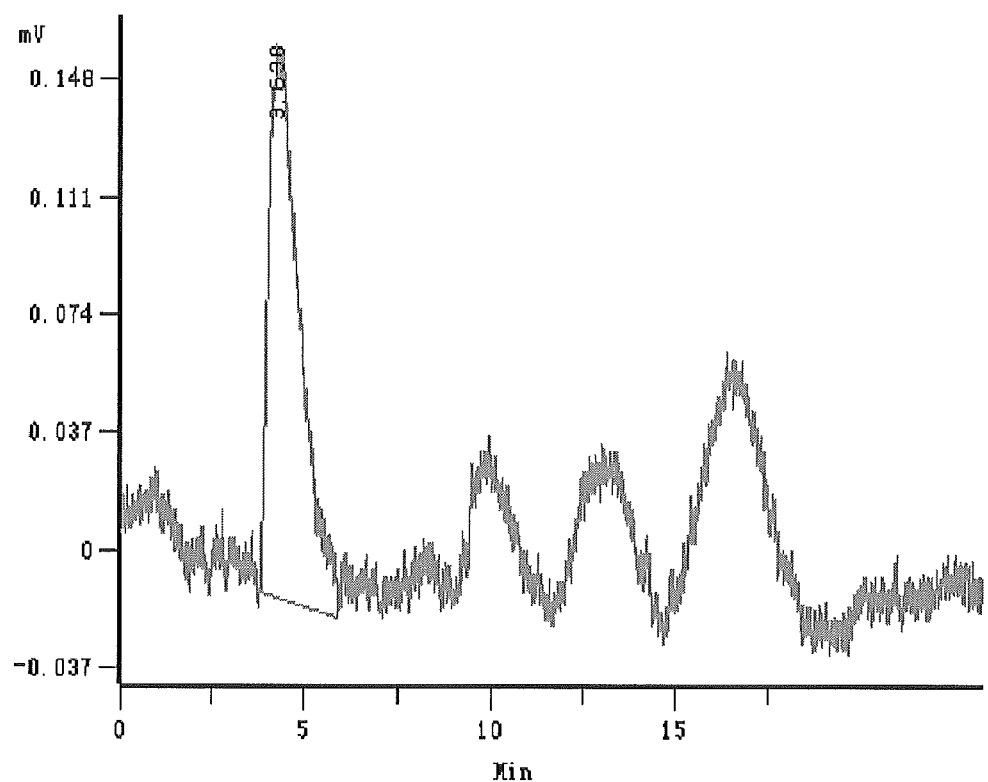
FIG. 1: HPLC chromatogram of BP-β-CD. Chromatographic conditions, Chromatographic column: phenyl-column (4.6 mm×250 mm, 5 μm); detection: display thermal analysis; mobile phase: methanol-water (1:10); column temperature: 25° C., sample concentration: 0.02 mg/ml, and sample injection quantity: 20 μl. HP-β-CD elution spectrum has a number of broad peaks under this chromatographic conditions, among them, the peak about 9 min is β-CD.

0.02 mol β-Cyclodextrin, 0.11 mol NaOH and 45 ml H2O were added into 3-neck round flask with isobarically funnel, reflux-condenser, and thermometer respectively; then stirred to dissolve completely and heated them to about 75° C.-80° C. and kept it in constant temperature, and then 0.08 mol 1,4-butane sultone was added within 3 hours, and continued to stir about 2 hours then cooled down to the normal temperature about 20° C.; 0.08 mol 1,2-Propylene Oxide was slowly pipetted for about 3 hours; continued to stir for 5 hours and PH value was adjusted to neutral with hydrochloric acid; filtered and the residual β-cyclodextrin and the resultant 1,2-propanediol and γ-hydroxy butyrate sodium were removed by filterate dialysis. After 8-10 times of dialysis, the mixture was dried under the condensed and pressure reduction condition, and the 25.7 g of white-like solid substance was obtained, yield of 111.7%. Each value of 1HNMR spectrum (See annex 12) was analyzed as follows:

| ppm | assignments of proton | Peak characteristics | Peak area | group of proton | DS |
|---|---|---|---|---|---|
| 1.05-1.06 | 3H: —CH₃ | d | 5.43 | Hydroxypropyl | 1.8 |
| 1.69 | 4H: —CH₂—CH₂— | s | 12.02 | sulfobutyl | 3.0 |
| 2.83-2.85 | 2H: —CH₂—SO₃X | d | 5.99 | Sulfobutyl | 3.0 |
| 3.38-3.91 | 3H: —O—CH₂—CH—; 2H: —O—CH₂— | m | 53.92 | Glucose ring | |
| 4.99-5.16 | 6H: C₂—H; C₃—H; C₄—H; C₅—H; 2C₆—H 1H: —C₁H— | m | 7.00 | Glucose ring | |

β-CD has seven C1—H (glucose ring C1) with chemical shift of 4.99-5.16 ppm; The integral of the characteristic peak area is 7, which indicates seven C1—H (i.e. one β-CD), then the area of the corresponding methyl-peak of the derivative (1.05-1.06 ppm)/3 is the total number of hydroxypropyl connected with methyl in each cyclodextrin (degree of substitution), the corresponding —CH2-CH2-group peak (1.69 ppm) area/4; and the corresponding —CH2-SO3X group peak (2.83-2.85 ppm) area/2 is the degree of substitution of sulfobutyl group connected in each cyclodextrin. As shown in above table, the degree of substitution of the synthesized product is respectively 1.8 of HP's average degree of substitution and 3.0 of Sulfobutyl's average degree of substitution, and was abbreviated as HP2-SBE3-β-CD.

Figure 13:
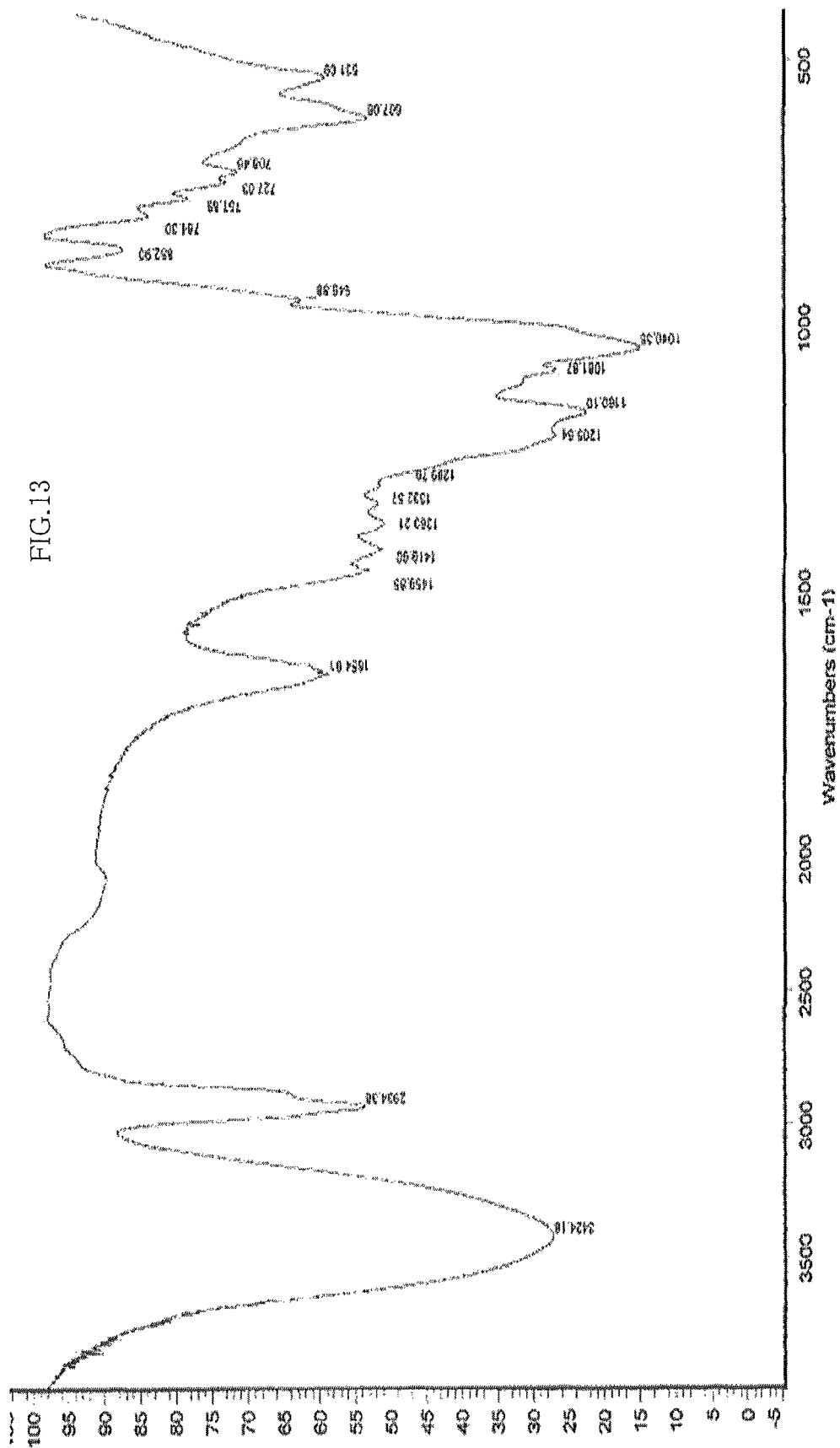
FIG. 13: HP2-SBE3-β-CD IR spectrum.

The values of IR (KBr) Spectrum (FIG. 13) are shown as follows:

| frequency (cm-1) | Functional group | Characteristics |
|---|---|---|
| 3424 | O—H | Primary and secondary hydroxyl groups of CD, strong absorption |
| 2934 | C—H | methylene of the branch chain, pinnacle |
| 1460 | C—H | methylene, bending |
| 1420 | —SO2—O | elongation |
| 1370 | C—H | methylene, bending |
| 1333 | S=O | elongation |
| 1206 | C—O—C | ether bond, elongation |
| 1160 | C—O—C/—SO2—O | elongation |
| 1082 | C—O/C—C | elongation |
| 1040 | C—O/C—C | elongation |
| 946 | α-1,4- | framework vibration |
| 853 | C-1 | group vibration |

Figure 14:
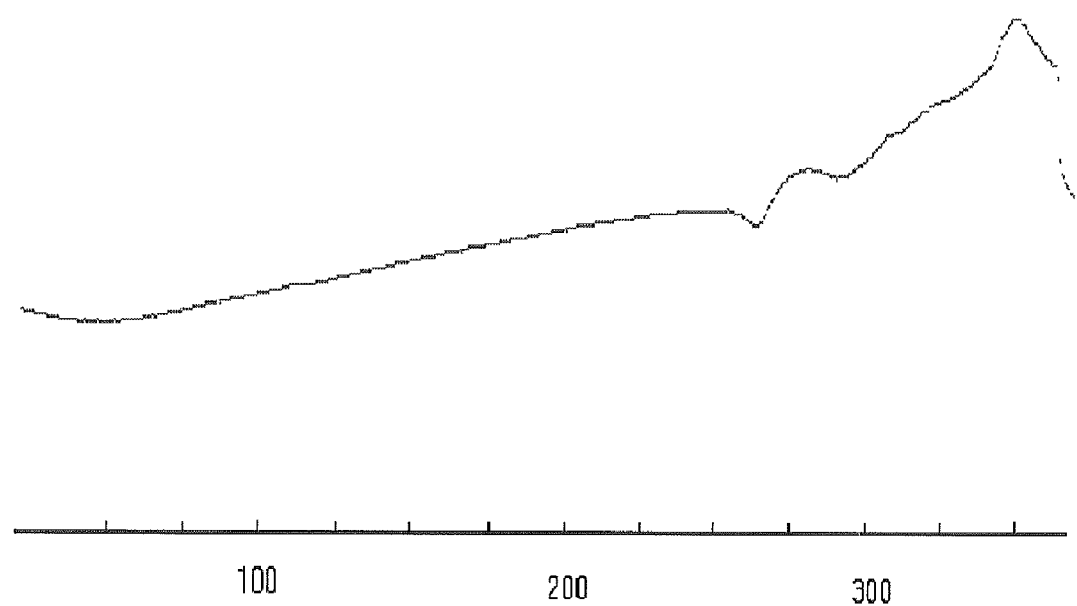
FIG. 14: HP2-SBE3-β-CD DSC spectrum.

DSC map (FIG. 14) Analysis: dehydration peak (weak): 50~90° C.; melting point: 263~290° C.; decomposition points: 345° C.

Other physiochemical parameters are as follows: average molecular weight M=1718 g/mol; water content: 5.0% (Bibliography: 2000 Pharmacopoeia Appendix VIII M Determination method of moisture-toluene); specific rotation: [α]=+107.97 (WZZ-2S/2SS digital automatic rotation spectrometer: Bibliography of Shanghai Precision Scientific Instrument Co., Ltd.: Specific rotation determination method 2000 Pharmacopoeia Appendix VI rotation determination method).

Preparation of HP2-SBE3-β-CD reference substance: the HP2-SBE3-β-CD synthesized was placed in an oven at 100° C., 72 h later, taken out and cooled down, kept in the dryer for future use. A few samples were precisely weighed, mixed with equal mols of benzoic acid (internal standard). D2O was used as solvent to determine the mixture 1HNMR spectrum; benzoic acid Ar—H and cyclodextrin nucleus C1—H peak area integration ratio (equal molar ratio=5:7) was adopted to calculate and calibrate HP2-SBE3-β-CD and the content=93.2% was obtained; by HPLC method, the residual cyclodextrin detected was 0.8% and the content of 1,2-propylene glycol and γ-hydroxybutyrate sodium were respectively 1.0% and 1.2 ppm, and then the compound was used as reference substance to determine the sample content of other hydroxypropyl sulfobutyl-β-Cyclodextrin.

EXAMPLE 2

0.02 mol β-Cyclodextrin, 0.04 mol NaOH and 90 ml 1120 were added into 3-neck round flask with isobarically funnel, reflux-condenser, and thermometer respectively; then stirred to dissolve completely and 0.03 mol 1,2-propylene oxide was slowly pipetted for about 2 hours when stirred at 20° C.; continued to stir for reacting for 6 hours, 0.3 mol NaOH was added, heated to about 75° C.~80° C., then 0.03 mol 1,4-Butane sultone was slowly pipetted for about 3 hours, continued to stir for reacting 5 hours, and then cooled to the room temperature, and PH value of the mixture was adjusted to neutral with hydrochloric acid; filtered and the residual β-cyclodextrin and the resultant 1,2-propanediol and γ-hydroxy butyrate sodium were removed by filterate dialysis. After 8-10 times of dialysis, the mixture was dried under the condensed and pressure reduction condition, and 25 g of white-like solid substance was obtained, yield of 108.7%. The average degree of substitution of hydroxypropyl was 1.2 and the average degree of substitution of sulfobutylether is 8.9 through 1HNMR validation, abbreviated as HP1-SBE9-β-CD.

Figure 15:
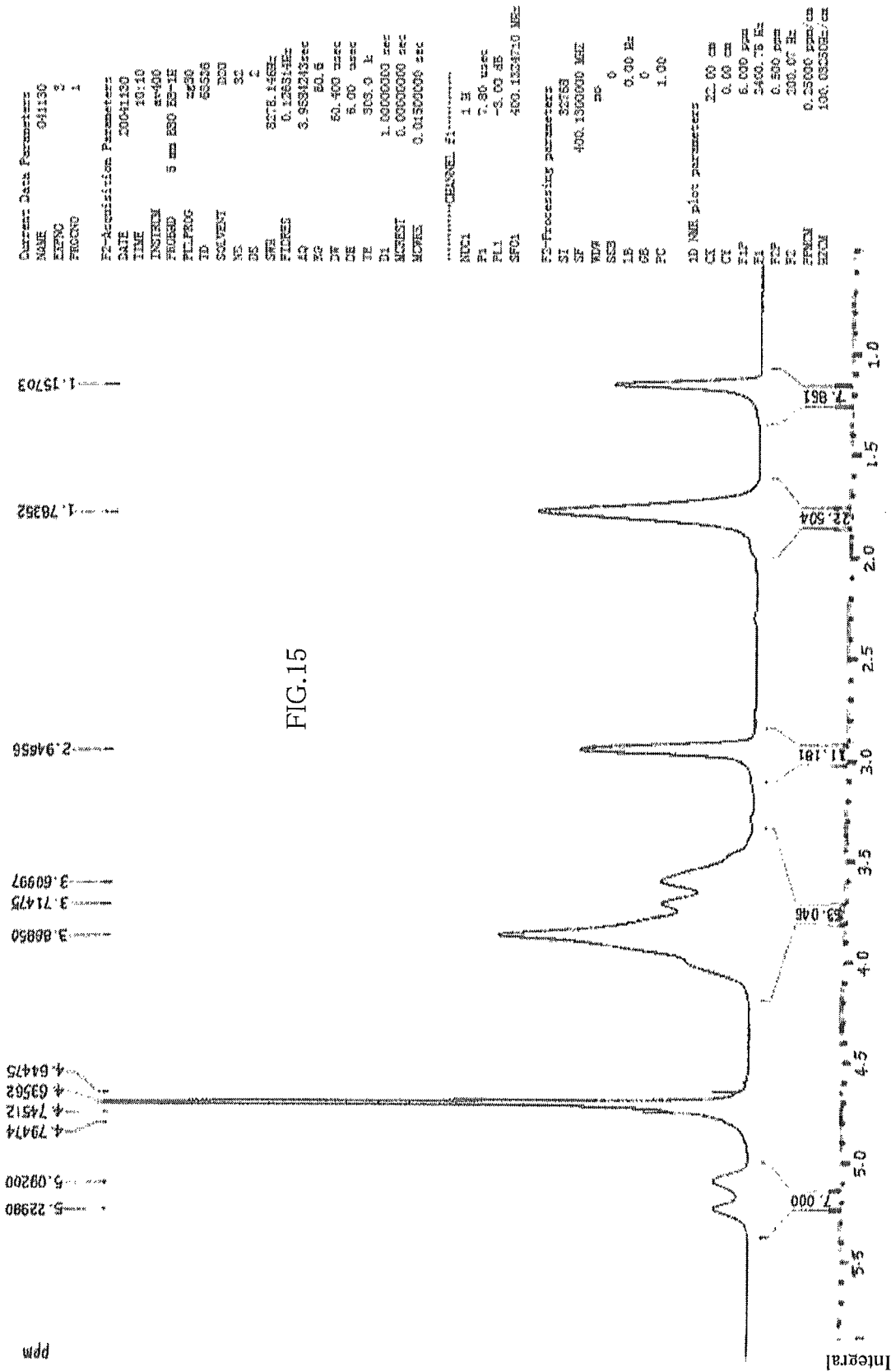
FIG. 15: HP3-SBE6-β-CD 1HNMR spectrum.
Figure 16:
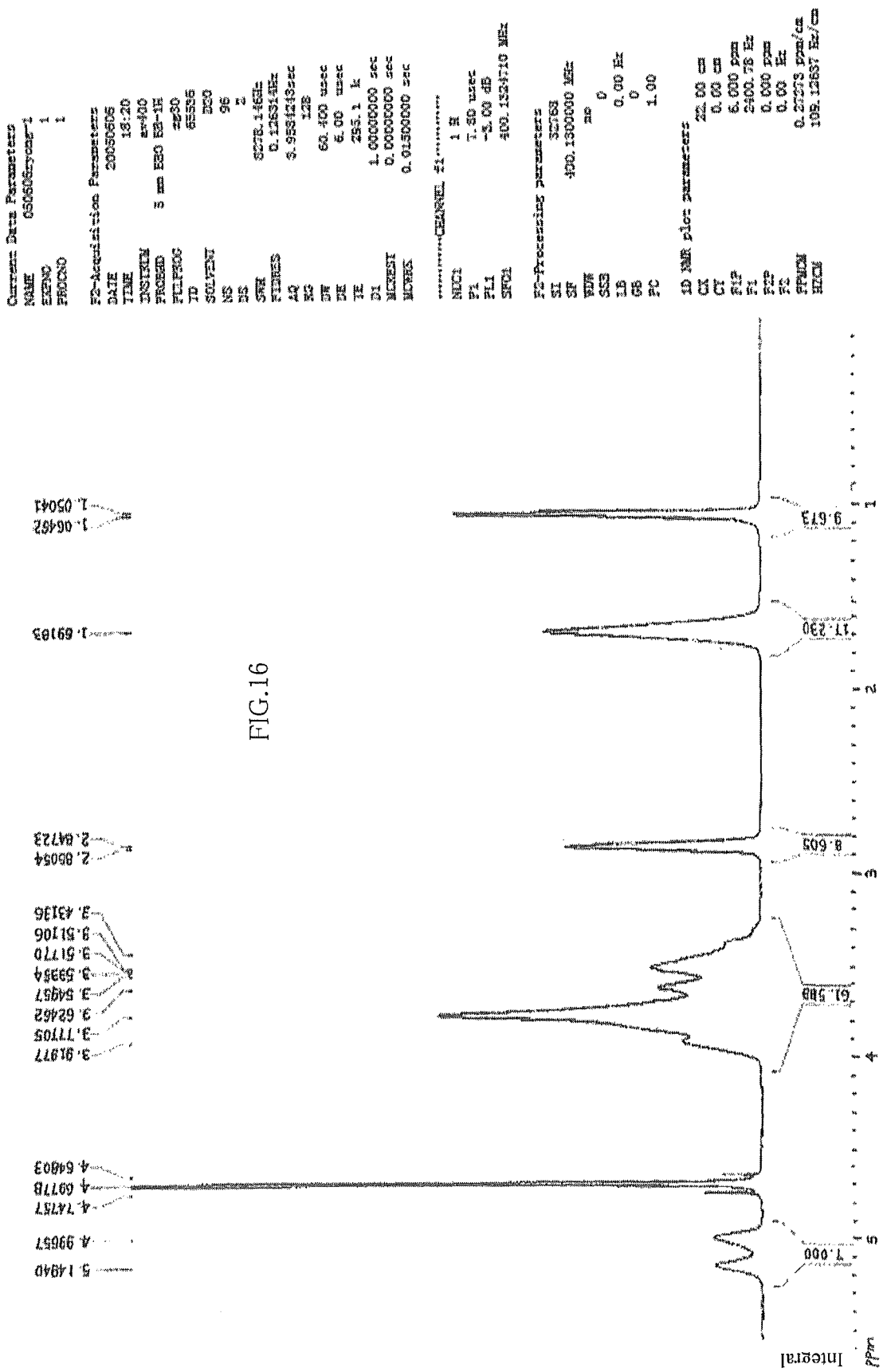
FIG. 16: HP3-SBE4-β-CD 1HNMR spectrum.

EXAMPLE 3 the procedure was carried out basically the same as example 1, but wherein, 70 ml of water was added, and the feeding quantity of NaOH, 1,4-butane sultone and 1,2-propylene oxide were 0.20, 0.16, 0.10 mol respectively, the final product yield is 105.5%. The average degree of substitution of hydroxypropyl was 5.6 and the average degree of substitution of sulfobutyl was 2.6 by 1HNMR validation (FIG. 15), abbreviated as HP3-SBE6-β-CD.

EXAMPLE 4 the procedure was carried out basically the same as example 1, but wherein, the feeding quantity of NaOH, 1,4-butane sultone and 1,2-propylene oxide were 0.15, 0.12, 0.115 mol respectively, the final product yield is 104.35%. The average degree of substitution of hydroxypropyl was 3.2 and the average degree of substitution of sulfobutyl was 4.3 by 1HNMR validation (FIG. 15), abbreviated as HP3-SBE4-β-CD.

EXAMPLE 5 the procedure was carried out basically the same as example 1, but wherein, 90 ml of water was added, and the feeding quantity of NaOH, 1,4-butane sultone and 1,2-propylene oxide were 0.08, 0.04, 0.26 mol respectively, the final product yield was 110.5%. The average degree of substitution of hydroxypropyl was 9.1 and the average degree of substitution of sulfobutyl was 1.1 by 1HNMR validation (FIG. 15), abbreviated as HP9-SBE1-β-CD.

EXAMPLE 4 the procedure was carried out basically the same as example 1, but wherein, the feeding quantity of NaOH, 1,4-butane sultone and 1,2-propylene oxide were 0.06, 0.04, 0.04 mol respectively, and 1,4-butane sultone was added to react for 5 h and 1,2-propylene oxide was added to react for 5 h. The final product yield was 101.36%. The average degree of substitution of hydroxypropyl was 1.3 and the average degree of substitution of sulfobutyl was 1.4 by 1HNMR validation (FIG. 15), abbreviated as HP1-SBE1-CD.

EXAMPLE 7-1 the procedure was carried out basically the same as Example 1, but, wherein, the base for the catalystic reaction is KOH, and the product of potassium salt of sulfobutyl group.

EXAMPLE 7-2 the procedure was carried out basically the same as Example 1, but, wherein, the base for the catalystic reaction is LiOH, and the product of lithium salt of sulfobutyl group.

EXAMPLE 8

Figure 2:
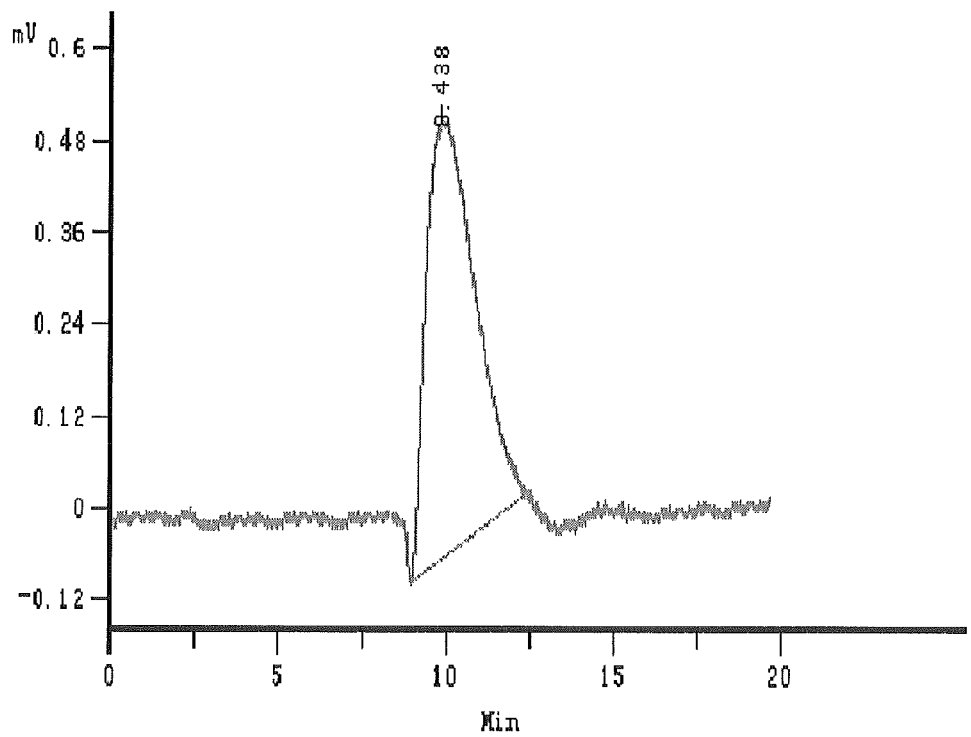
FIG. 2: HPLC chromatogram of β-CD. Chromatographic conditions are the same as that of FIG. 1. β-CD elution spectrum has a broad peak at about 9 min under the chromatographic condition.
Figure 3:
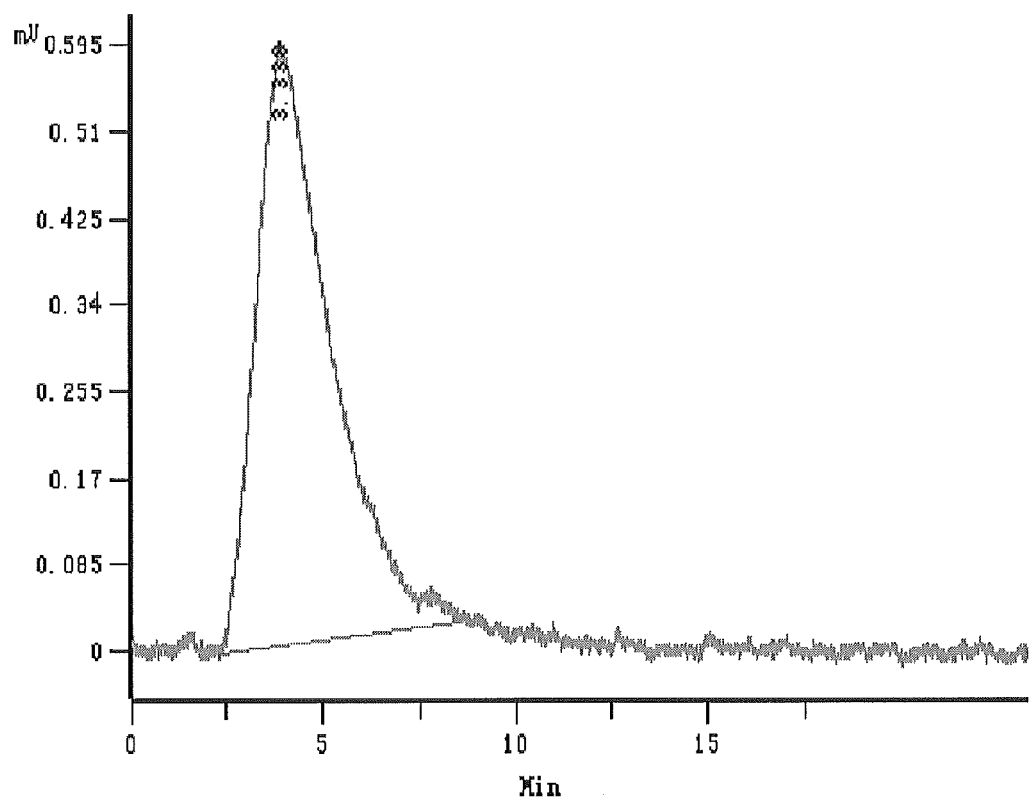
FIG. 3: HPLC chromatogram of HP2-SBE3-β-CD. Chromatographic conditions are the same as that of FIG. 1. Sulfobutyl group was introduced to HP2-SBE3-β-CD on the basis of HP-β-CD structure, which make cyclodextrin polarity increase, easy elution, presenting a large single-broad peak around 3.4 min.

Identify that hydroxypropyl-sulfobutyl-, cyclodextrin is the cyclodextrin mixed-substituted by hydroxypropyl and sulfobutyl group, rather than the simple mixture of two or three selected among β-CD, hydroxypropyl-β-CD and sulfobutyl-β-cyclodextrin by HPLC method.

chromatographic conditions chromatographic column: phenyl-group column (4.6 mm×250 mm, 5 μm); detection: Display thermal analysis; the mobile phase: methanol-water (1:10); column temperature: 25° C. Precisely weigh 0.1 g of HP-β-CD, β-CD and HP2-SBE3-β-CD respectively, dissolve them with the mobile phase and adjust then to the constant 5 ml for sampling; the sample size: 20 μl. HPLC spectra of HP-β-CD, β-CD and HP2-SBE3-β-CD are shown in FIGS. 1, 2 and 3 respectively.

EXAMPLE 9

Identify that hydroxypropyl-sulfobutyl-β-cyclodextrin is the cyclodextrin mixed-substituted by hydroxypropyl and sulfobutyl group, rather than the simple mixture of two or three selected among β-CD, hydroxypropyl-β-CD and sulfobutyl-1 cyclodextrin by dialysis method.

5 g of HP-β-CD (average degree of substitution: 6) and 5 g of HP2-SBE3-β-CD were added with 10 times of water to prepare the solution, dialyzed for 5 h with dialysis tubes (MWCO3000), and then dried under the condensed and pressure reduction condition, finally 0.3 g and 4.7 g white solid powder were obtained. Then the dialysis loss rate was calculated, 94% for HP-β-CD, 6% for HP2-SBE3-β-CD.

EXAMPLE 10

Determination of Purity of Hydroxypropyl-Sulfobutyl-β-Cyclodextrin

1. Analysis and Detection of the Residual β-CD by HPLC Method
1) chromatographic conditions: chromatographic column: phenyl-group column (4.6 mm×250 mm, 5 μm); detection: Display thermal analysis; mobile phase: water; column temperature: 25° C.
2) Preparation of solution
Preparation of reference solution: 0.15 g β-CD was precisely weighed. The mobile phase solution was adjusted to the constant volume of 10 ml as the mother liquor a. Then 1 ml of mother liquor was precisely fetched to dissolve the β-CD and adjusted to the constant volume of 10 ml, which is used as the reference solution.

Preparation of sample solution: 1 g HP2-SBE3-β-CD was precisely weighed, dissolved with mobile phase and adjusted to the constant volume of 10 ml, used as the sample solution.

3) Determination: 20 ul of the above reference solution and 20 ul of sample solution were fetched for sampling detection, and the chromatogram was obtained. The peak area of β-CD among the samples should be less than the peak area of the reference solution (see FIG. 4 for the sample solution).

Figure 4:
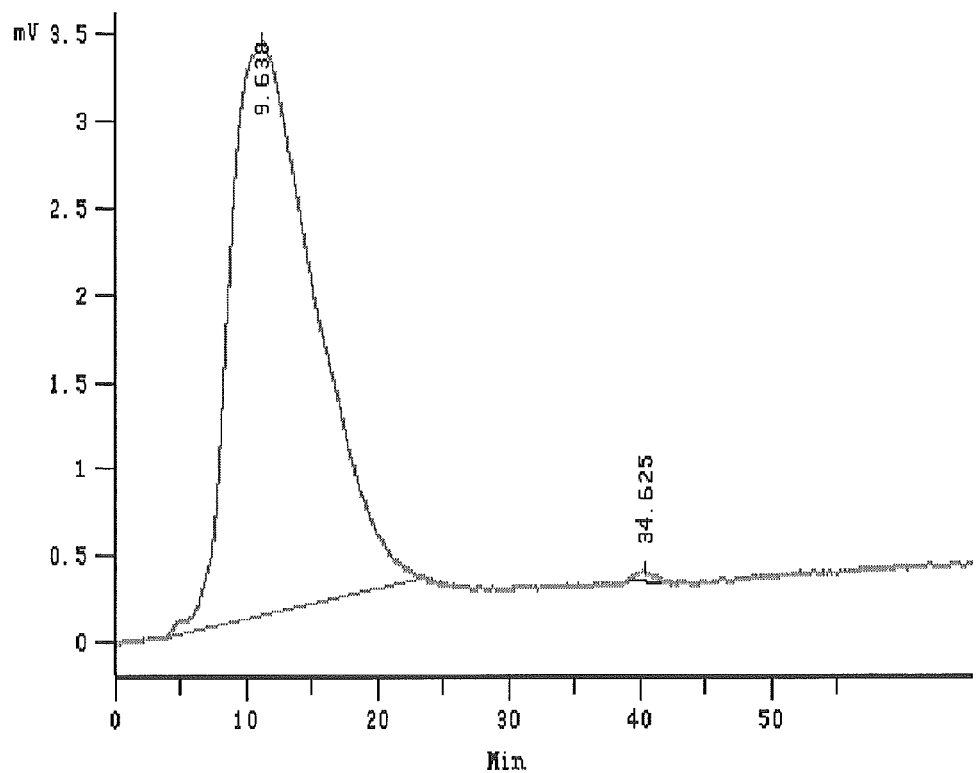
FIG. 4: An HPLC Detection chromatogram of β-CD residue in HP2-SBE3-β-CD. Chromatographic conditions: Chromatographic column: phenyl-column (4.6 mm×250 mm, 5 μm); detection: display thermal analysis; mobile phase: water, column temperature: 25° C., among them, the retention time for HP2-SBE3-β-CD is 9.6 min, and the retention time for β-CD is 34.6 min.
Figure 5:
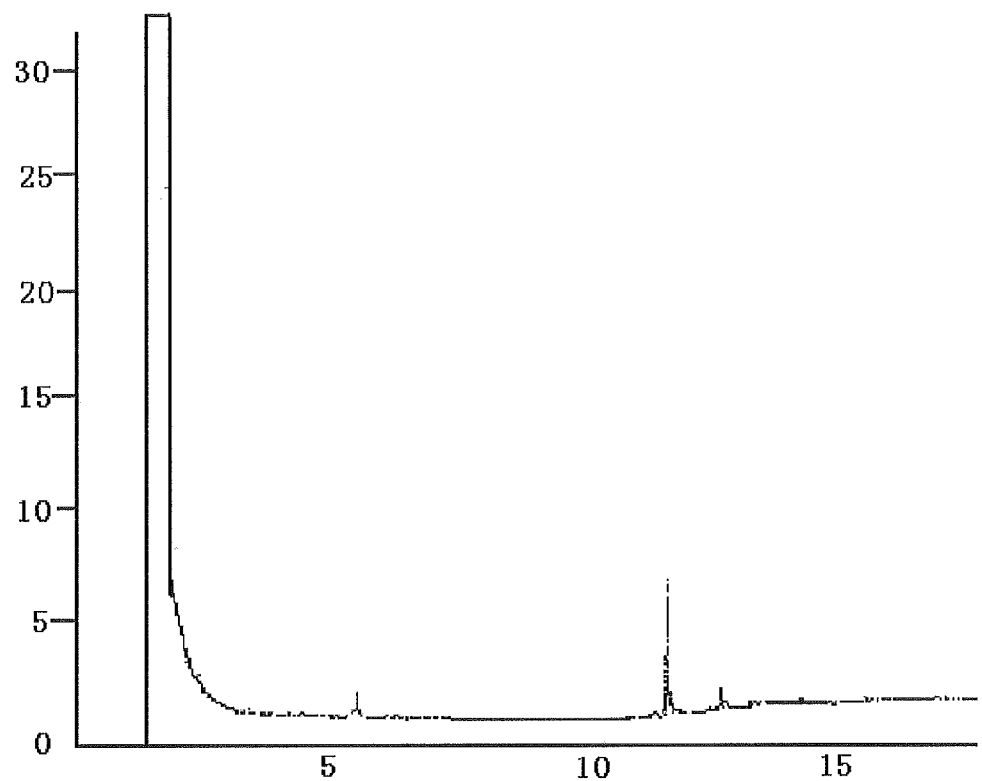
FIG. 5: The chromatogram of the content of γ-hydroxybutyrate sulfonate (calculated by 1,4-Butane sultone) and 1,2-propylene glycol in HP2-SBE3-β-CD by GC method. Among them, the retention time for 1,2-propanediol is 5.8 min, the retention time for 1,4-Butane sultone is 12.4 min.
Figure 6:
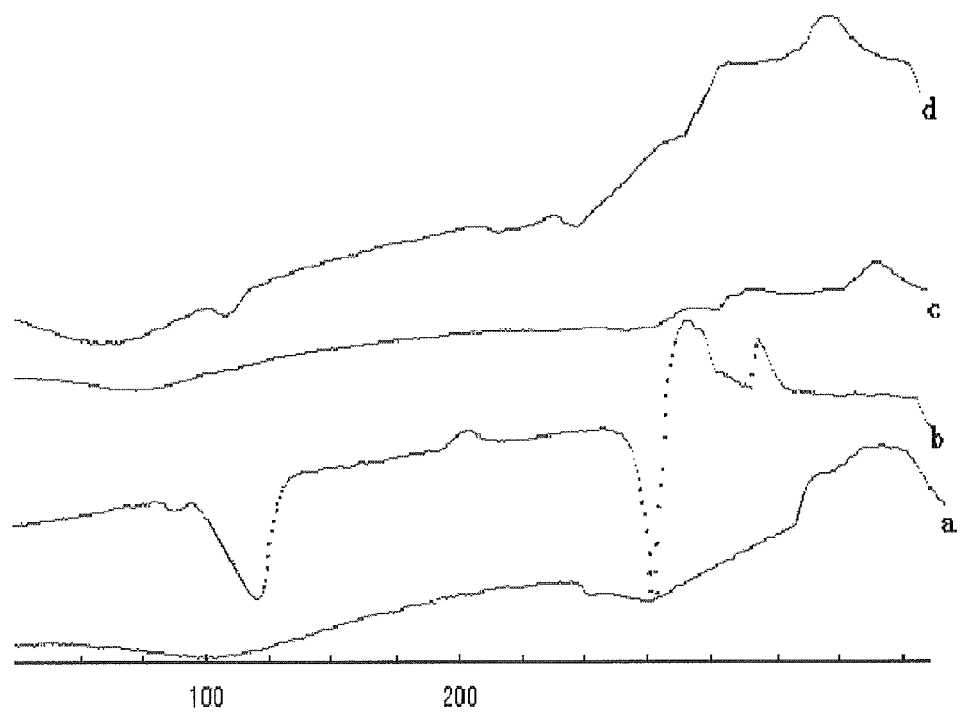
FIG. 6: Display thermal analysis chart of prazosin hydrochloride. Where, a represents HP4-SBE2-β-CD; b represents prazosin hydrochloride; c represents the inclusion of HP4-SBE2-β-CD and prazosin hydrochloride; d represents physical mixture of HP4-SBE2-β-CD and prazosin hydrochloride. It can be shown from d, the physical mixture maintains water peak and melting peak of prazosin hydrochloride, and is a basically simple accumulation of prazosin hydrochloride and HP4-SBE2-β-CD; and from c, it can be shown that the water peak of prazosin hydrochloride disappeared, and each peak position (temperature) and shape (thermal effect) have changed, which demonstrated that the inclusion complex has been formed.
Figure 7:
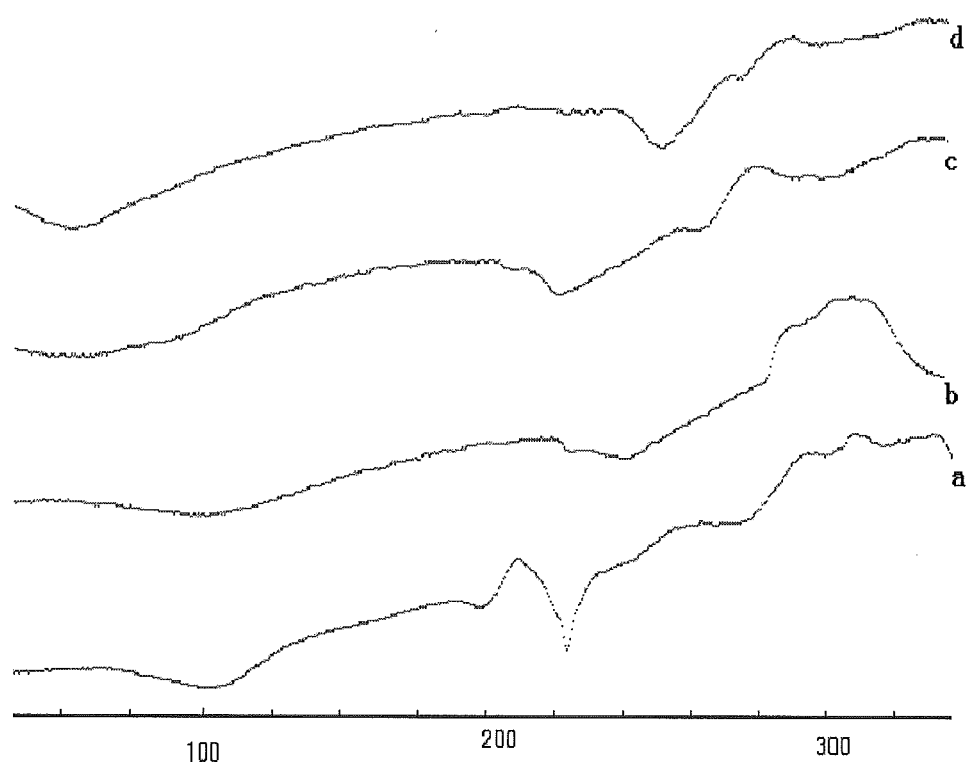
FIG. 7: Display thermal analysis chart of Ibuprofen. Where, a represents ibuprofen; b represents HP4-SBE2-β-CD; c represents physical mixture of HP4-SBE2-β-CD and ibuprofen; d represents inclusion of HP4-SBE2-β-CD and ibuprofen. It can be shown from FIG. C, the physical mixture maintains water peak of ibuprofen, which is a basically simple accumulation of ibuprofen and HP4-SBE2-β-CD; from d, we can see that the water peak of ibuprofen disappeared, and each peak position (temperature) and shape (thermal effect) changed, which demonstrated that the inclusion complex has been formed.
Figure 8:
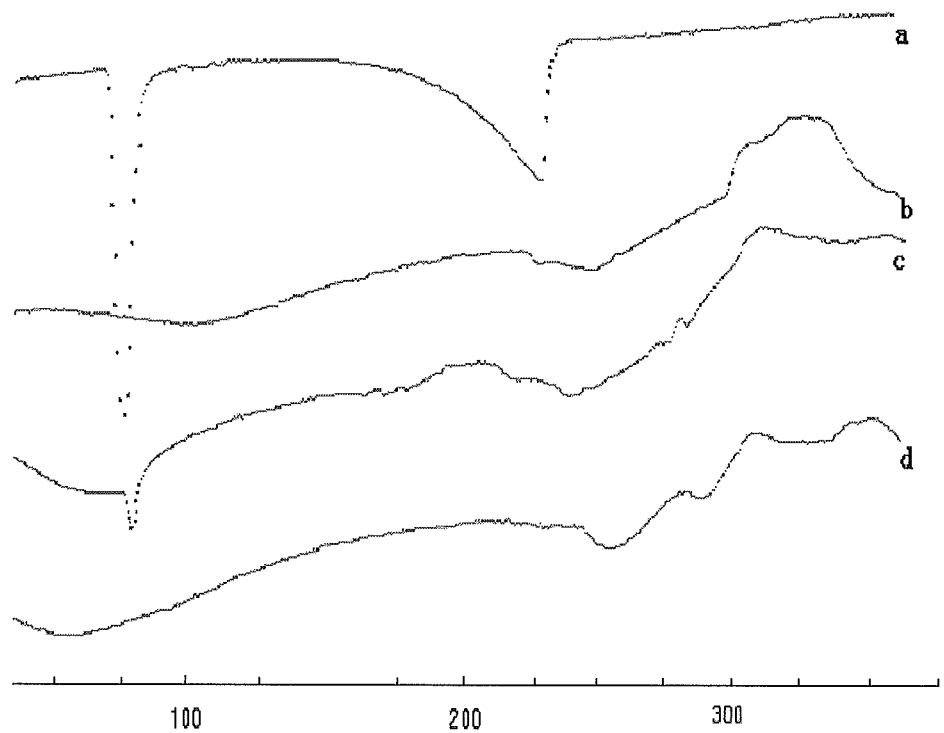
FIG. 8: Display thermal analysis chart of puerarin. Where, a represents puerarin; b represents HP4-SBE2-β-CD; c represents physical mixture of HP4-SBE2-β-CD and puerarin; d represents inclusion of HP4-SBE2-β-CD and puerarin. It can be shown from FIG. C, the physical mixture is a basically simple accumulation of puerarin and FP4-SBE2-β-CD; from d, we can see that each puerarin peak position (temperature) and shape (thermal effect) changed, which demonstrated that the inclusion complex has been formed.
Figure 9:
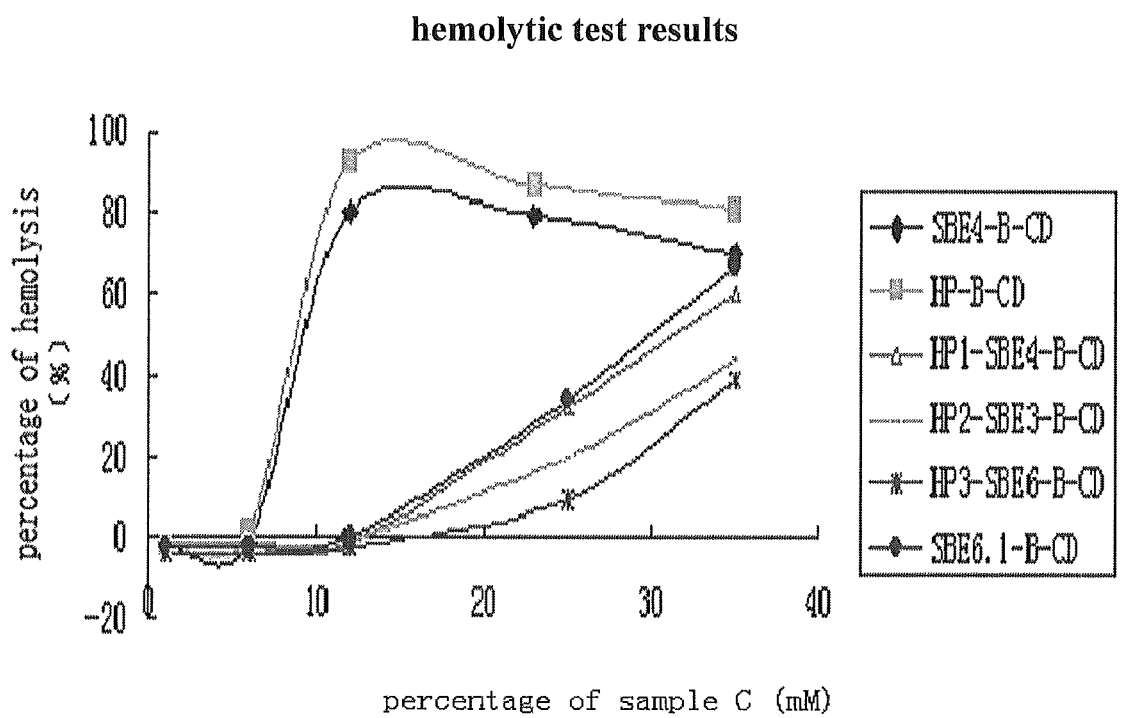
FIG. 9: hemolytic test results: in comparison with HP-β-CD, SBE7-β-CD and SBE4-β-CD, determine the percentage of hemolysis of HP1-SBE4-β-CD, HP3-SBE6-β-CD and HP2-SBE3-β-CD at the concentration of 1,6,12,25 and 35 mM. As shown in the figure, the percentage of hemolysis of HP1-SBE4-β-CD, HP3-SBE6-β-CD, HP2-SBE3-β-CD at above concentration is much lower than the percentage of HP-β-CD, and the percentage of hemolytic is basically in a linear rising. The percentage of hemolytic of HP2-SBE3-β-CD and HP3-SBE6-β-CD at concentration of 35 mM is less than 50%. β-CD at all concentrations shows high-hemolysis. Degree of Hemolysis: β-CD>HP-β-CD>HP1-SBE4-β-CD>HP3-SBE6-β-CD>HP2-SBE3-β-CD.
Figure 10:
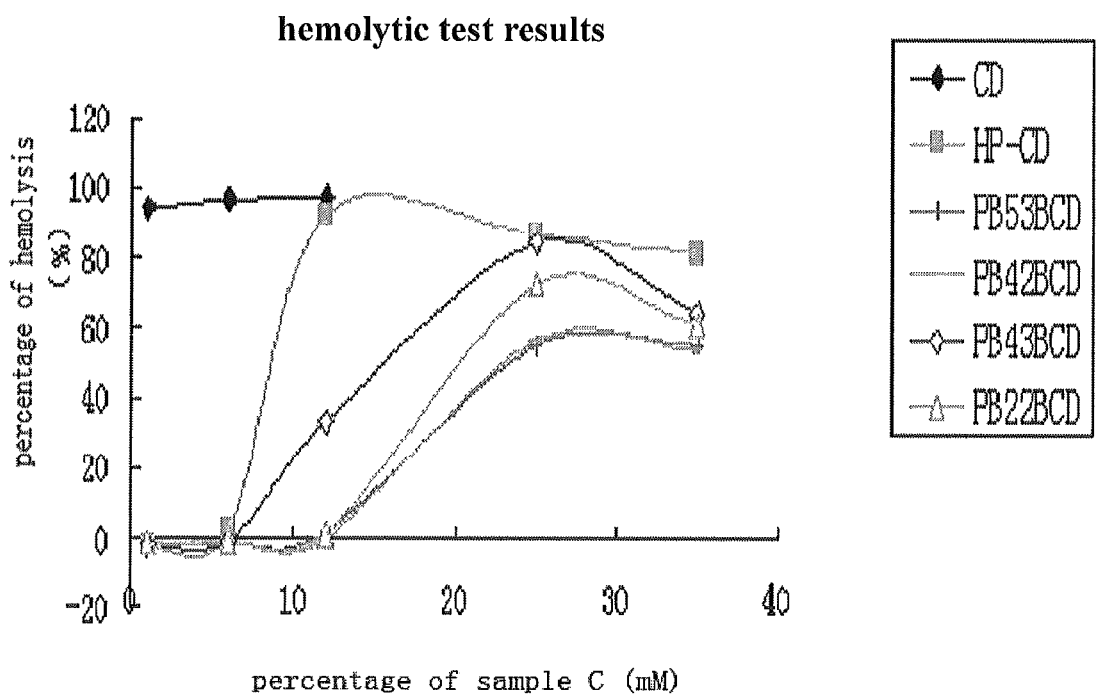
FIG. 10: hemolytic test results: in comparison with HP-β-CD and β-CD, determine the percentage of hemolysis of HP4-SBE3-β-CD, HP2-SBE2-β-CD, HP4-SBE2-β-CD and HP5-SBE3-β-CD at the concentration of 1, 6, 12, 25 and 35 mM. The percentage of hemolysis of all compounds increases with the increase of the concentration and each sample reaches the maximum percentage of hemolysis at concentration of 27 mM and then decreases to close to the hemolysis change of HP-β-CD. At all concentrations, the resultant product obtained herein is lower than that of HP-β-CD. Degree of hemolysis: β-CD>HP-β-CD>HP4-SBE3-β-CD>HP2-SBE2-β-CD>HP4-SBE2-β-CD>HP5-SBE3-β-CD.
Figure 11:
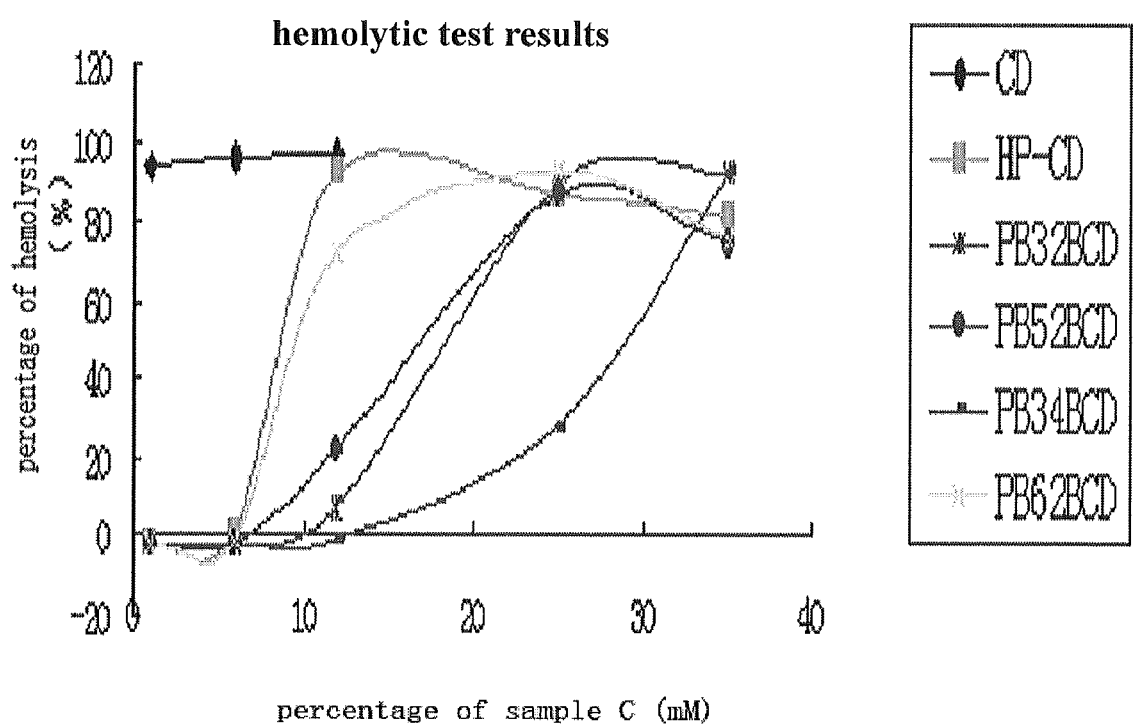
FIG. 11: hemolytic test results: in comparison with HP-β-CD and β-CD, determine the percentage of hemolysis of HP6-SBE2-β-CD, HP5-SBE2-β-CD, HP3-SBE2-β-CD and HP3-SBE4-β-CD at the concentration of 1, 6, 12, 25 and 35 mM. When the concentration is lower than 25 mM, the percentage of hemolysis of each sample is lower than that of HP-β-CD; when the concentration is lower than 25 mM, the sequence of hemolysis degree: β-CD>HP-β-CD>HP6-SBE2-β-CD>HP5-SBE2-β-CD>IP3-SBE2-β-CD>HP3-SBE4-β-CD.
Figure 12:
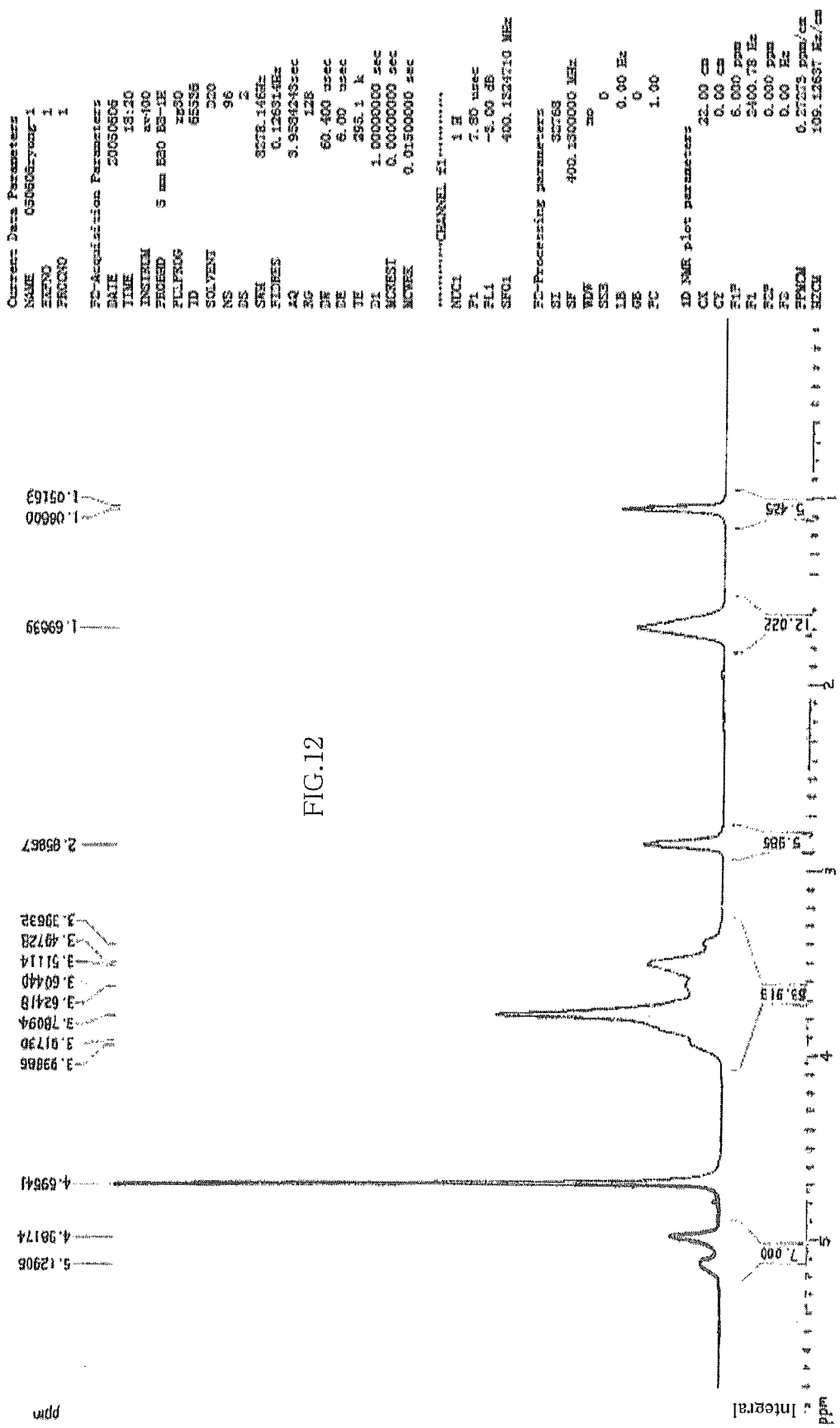
FIG. 12: HP2-SBE3-β-CD 1HNMR spectrum.

4) System suitability test: 20 ul of the above reference solution was fetched for sampling detection, and the chromatogram was obtained. The number of theoretical plates is 2600 calculated by β-CD, and the degree of separation with the HP2-SBE3-β-CD sample peak is 3.78 (FIG. 4).

5) Detection limit: β-CD mother liquor was diluted for 300 times, and the minimum detection limit of β-CD is 1 ug based on S/N=3.

2. Analysis and Detection of γ-Hydroxybutyrate Sulfonate and 1,2-Propanediol by GC Method 1) chromatographic conditions: chromatographic system: Saturn GC3800; chromatographic column: DB-5 quartz capillary column, 30 m×0.25 mm×0.25 μn; detector: hydrogen flame ionization detector (FID); Temperature: detector temperature 250° C.; Carrier gas: N2.

2) Preparation of solution

Preparation of reference solution: 20 mg of 1,4-butyl sultone was precisely weighed, heated for 1 h with pure water, then cooled down and adjusted to the constant volume of 50 ml. 5 ml of the above solution was fetched and diluted to 100.00 ml. Then the 2.00 ml of the diluted solution was added to 50 mg of 1,2-propanediol, and dissolved with pure water till 20 ml. Then the mixture was extracted by chloroform (extracted with 10 ml of chloroform each time, for three times), the organic phase was combined, and the chloroform was slightly removed till dried, then the residual substance was dissolved with water, and adjusted to the constant volume of 2.00 ml with water, thus, the reference solution containing 0.02 mg/ml 1,4-butyl sultone and 25 mg/ml 1,2-propanediol was prepared.

Preparation of sample solution: 10 g of sample product was dissolved with 10 ml of pure water (by adding 1-2 drops of 2 MH2SO4 solution), added with 10 ml of chloroform for extraction each time, for three time in total, the organic phase was combined, and the solvent was removed carefully, the residual substance was dissolved with pure water and adjusted to the constant volume of 1.00 ml, and thus the sample solution was prepared.

3) Determination: 5 ul of reference solution and 5 ul of sample solution were fetched for sample injection respectively. The peak area of each peak for the sample should be less than the peak area of the corresponding peak of the reference products.

4) System suitability test: Under the above chromatographic conditions, 5 ul of sample solution was injected and the chromatogram was obtained. The number of theoretical plates was 22,200 calculated by 1,4-butyl sultone, and the degree of separation with propylene glycol>1.5, and the degree of separation with chloroform is 16.7 (Pure chloroform 1 ul+sample solution 4 ul for sample injection).

5) Minimum detection limit: The reference solution was diluted for five times, the peak height was twice as the noise, therefore the minimum detection limit of 1,4-butyl sultone is 4.0 ppm. Samples are concentrated for 10 times, which is equivalent to the minimum content of 1,4-butyl sultone that can be detected is 0.4 ppm (4/10=0.4 ppm).

EXAMPLE 11

Assay of Hydroxypropyl-Sulfobutyl-β-CD

Reverse Phase-HPLC(RP-HPLC) Method

Chromatographic condition: chromatographic column: phenyl-group column (4.6 mm×250 mm, 5 μm); detection: Display thermal analysis; mobile phase: methanol-water (1:10); column temperature: 25° C. 0.1 g of HP2-SBE3-β-CD reference substance was precisely weighed, and dissolved by mobile phase and adjusted to the constant volume of 5 ml for sample injection; the sampling amount: 20 ul, and the chromatogram is plotted (FIG. 3).

Chromatographic condition: chromatographic column: C18 (4.6 mm×250 mm, 5 μm); detection: Display thermal analysis; mobile phase: methanol-water (1:10); column temperature: 40° C. 0.5 g of HP2-SBE3-β-CD reference substance was precisely weighed, and dissolved by mobile phase and adjusted to the constant volume of 10 ml for sample injection; the sample injection amount: 20 ul, and the chromatogram is plotted.

Normal Phase HPLC Method

Figure 17:
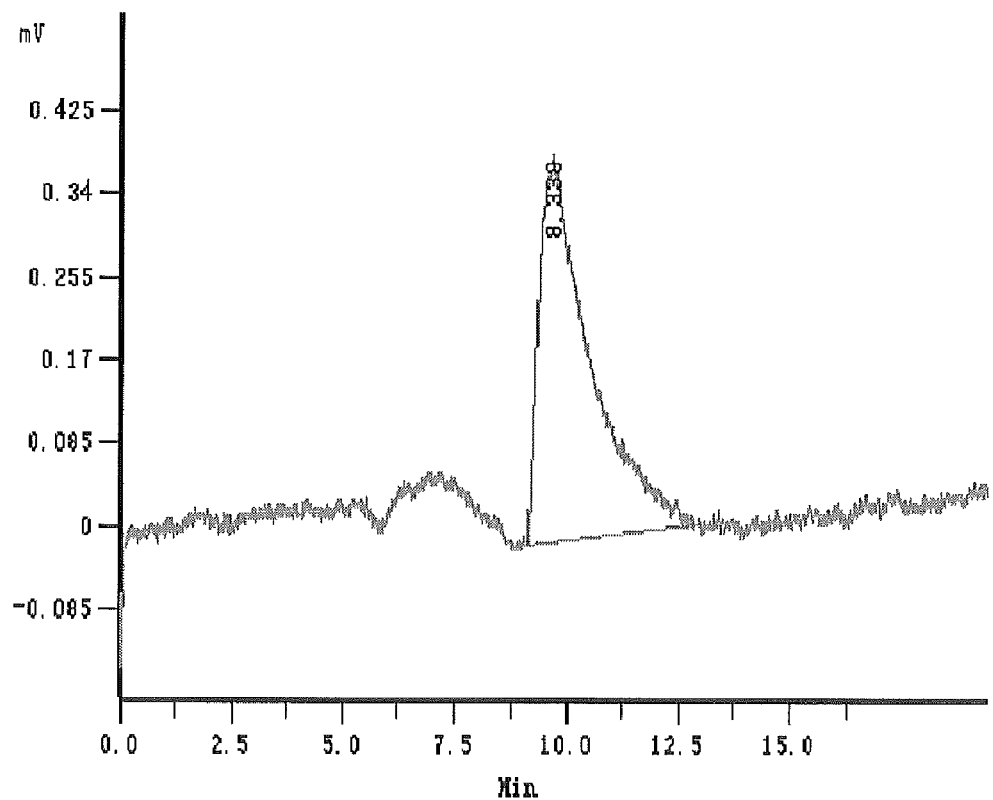
FIG. 17: HP2-SBE3-β-CD HPLC chromatogram: chromatographic conditions: SiO2 (4.6 mm×250 mm, 5 μm) chromatographic column; display thermal analysis; acetonitrile mobile phase; column temperature: 25° C. Sample concentration: 0.001 g/ml.
Figure 18:
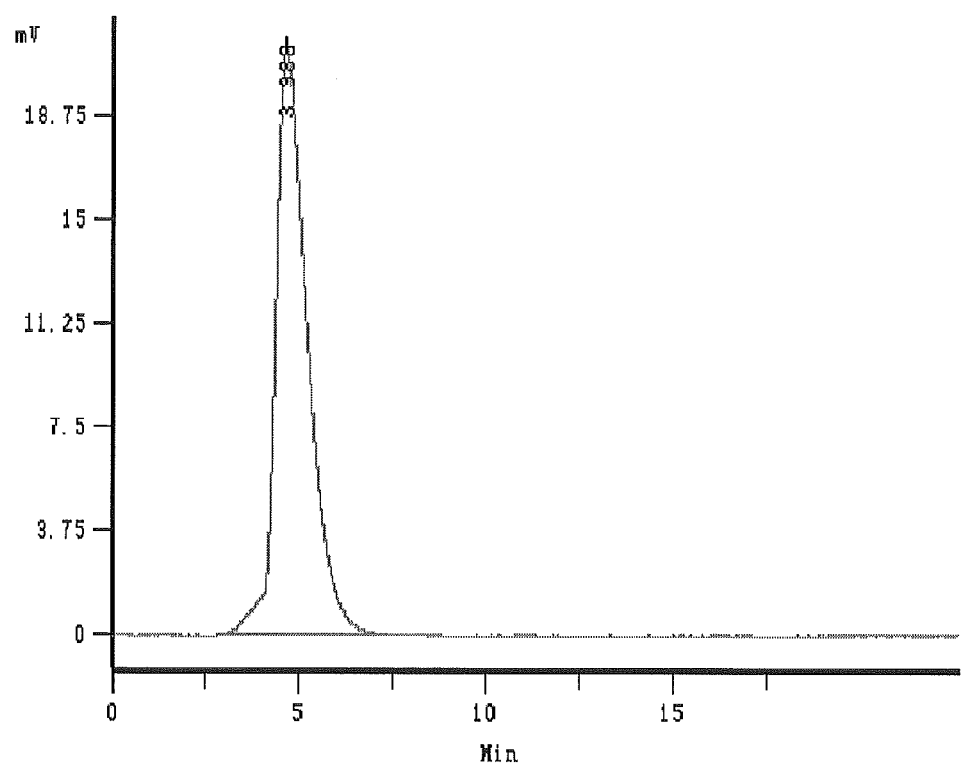
FIG. 18: HP2-SBE3-β-CD HPLC chromatogram: chromatographic conditions: SiO2 (4.6 mm×250 mm, 5 μm) chromatographic column; display thermal analysis; methanol mobile phase; column temperature: 25° C. Sample concentration: 0.01 g/ml.
Figure 19:
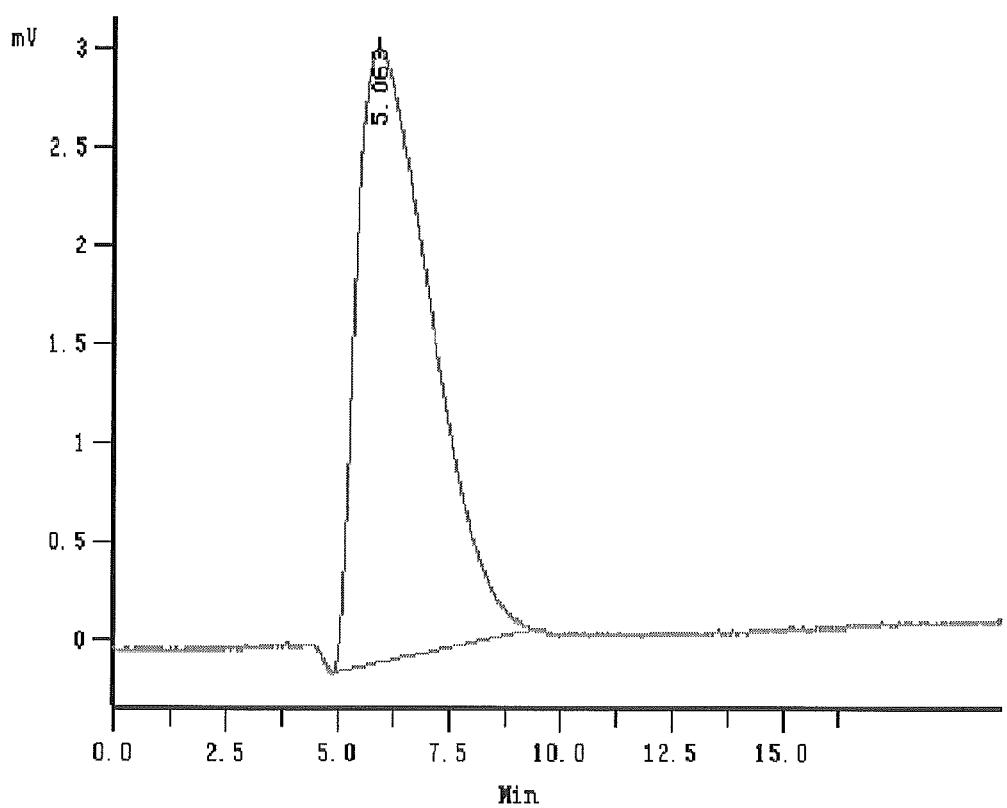
FIG. 19: HP2-SBE3-β-CD HPLC chromatogram: chromatographic conditions: SiO2 (4.6 mm×250 mm, 5 μm) chromatographic column; display thermal analysis; ethanol mobile phase; column temperature: 25° C. Sample concentration: 0.01 g/ml.

Chromatographic condition: chromatographic column: SiO2 (4.6 mm×250 mm, 5 μm); detection: display thermal analysis; mobile phase: acetonitrile; column temperature: 25° C. 0.01 g of HP2-SBE3-β-CD reference substance was precisely weighed, and dissolved by mobile phase and adjusted to the constant volume of 10 ml for sample injection; the sample injection amount: 20 ul, and the chromatogram is plotted (FIG. 17).

chromatographic column: SiO2 (4.6 mm×250 mm, 5 μm); detection: display thermal analysis; mobile phase: methanol; column temperature: 25° C. 0.1 g of HP2-SBE3-β-CD reference substance was precisely weighed, and dissolved by mobile phase and adjusted to the constant volume of 10 ml for sample injection; the sample injection amount: 20 ul, and the chromatogram is plotted (FIG. 18).

chromatographic column: SiO2 (4.6 mm×250 mm, 5 μm); detection: display thermal analysis; mobile phase: ethanol; column temperature: 25° C. 0.1 g of HP2-SBE3-β-CD reference substance was precisely weighed, and dissolved by mobile phase and adjusted to the constant volume of 10 ml for sample injection; the sampling amount: 20 ul, and the chromatogram is plotted (FIG. 19).

According to the above assay chromatographic conditions, the preferable assay method is as follows:

1) chromatographic condition: chromatographic column: phenyl-group column (4.6 mm×250 mm, 5 μm); detection: display thermal analysis; mobile phase: methanol-water (1:10); column temperature: 25° C. 0.5 g of HP2-SBE3-βCD reference substance was precisely weighed, and dissolved by mobile phase and adjusted to the constant volume of 10 ml for sample injection; the sample injection amount: 20 ul.

2) Preparation of solution

Preparation of standard solution: 0.5 g of reference substance was precisely weighed (qualified for purity test), dissolved with mobile phase and adjusted to the constant volume of 10 ml, and the standard solution is prepared.

Preparation of sample solution: 0.1 g of unknown sample was precisely weighed, dissolved by mobile phase and adjusted to the constant volume of 10 ml, and the sample solution is prepared.

3) Establishment of standard curve: the standard solution was diluted for 2, 5, 10, 20, 50 times respectively for sample injection detection. Plot linear regression of concentration C against peak area A, and the regression equation A=5928C−1368, r2=0.9948 is obtained, which indicated that when the sample injection quantity is within the scope of 0.02~1 mg, the linear relation is good.
4) Determination: the sample solution is fetched, and injected for 20 ul sample solution to obtain the peak area, then the actual measured concentration is calculate by the regression equation.
5) Minimum detection limit: the standard solution was diluted for 200 times to obtain the minimum detection limit of the samples of 5 ug calculated by S/N=10.

EXAMPLE 12

Inclusion of Hydroxypropyl-Sulfobutyl-β-Cyclodextrin and Cationic Drugs-Prazosin Hydrochloride HP4-SBE2-β-CD (10 g) was precisely weighed and mixed with the pure water (10 ml), heated, then added with 3.11 g of prazosin hydrochloride, after fully mixed for 3 h under stirring, then filtered, dried under pressure reduction and normal temperature condition, thus white solid inclusion complex is prepared.
1) Determination of Inclusion Constant of Prazosin Hydrochloride and Hydroxypropyl-Sulfobutyl-β-Cyclodextrin PBS of PH6.86 was used to prepare hydrochloride prazosin dilute solution, and this dilute solution was used to prepare HP4-SBE2-β-CD sample solution. Assume that the UV absorption value (A0) of prazosin hydrochloride solution under the wavelength of 250 nm was A0, and the sample concentration of HP4-SBE2-β-CD was changed to $1.67 \times 10^{-4} \sim 8.94 \times 10^{-4}$ mol/L, then the UV absorption (A1-An) under different HP4-SBE2-β-CD concentration systems was obtained by the formula $1/\Delta A = 1/(\Delta \epsilon \, K_a \, [G]_0 [CD]_0) + 1/\Delta \epsilon \, [G]_0$ (Δ A: Change of UV absorption values of prazosin hydrochloride, [CD]0: total concentration of the sample, [G]0: concentration of prazosin hydrochloride, Δε: the difference of molar absorptivity before and after inclusion). A line by $1/\Delta A$ against $1/[CD]_0$ was plotted, and the inclusion constant Ka of prazosin hydrochloride/HP4-SBE2-β-CD can be obtained according to the value of intercept/slope.
2) Display Thermal Analysis Validation Test of Inclusion Complex 5.0 mg of prazosin hydrochloride, HP4-SBE2-β-CD, physical mixture of prazosin hydrochloride and HP4-SBE2-β-CD and prazosin hydrochloride inclusion complex of HP4-SBE2-β-CD samples were weighed respectively, and display thermal analysis by scanning was conducted: reference: Al2O3, range: ±50 μV, temperature rise range: 40° C.~400° C., rate of heat rise: 10° C./min, and the DTA spectrum was thus obtained.
3) Solubilizing Test of Prazosin Hydrochloride Appropriate amount of prazosin hydrochloride was precisely weighed, dissolved with pH6.86 phosphate buffer solution and adjusted to the constant volume, then diluted to different multiples, then measure the UV absorptivity A under 250 nm. The standard curve was plotted by A against concentration C (μg/mL) to obtain C=9E-06 A+8E-08 R2=1.0000. Different degrees of substitution of hydroxypropyl-sulfobutyl-β-CD: HP2-SBE3-β-CD, HP3-SBE6-β-CD, HP6-SBE2-β-CD, were prepared to the solutions of concentration 10%, then added with excessive amount of prazosin hydrochloride, oscillated for 12 h at 25° C.±1° C. to reach a saturation balance, filtered, and then fetched of appropriate amount of filtrate, diluted by buffer solution, then the photoabsorption intensity was measured at 250 nm. The solubility and solubilization multiples of different degrees of substitution of hydroxypropyl-sulfobutyl-β-CD for the prazosin hydrochloride were obtained according to the standard curves (see Table 7).

EXAMPLE 13

Inclusion of Hydroxypropyl-Sulfobutyl-β-Cyclodextrin and Anionic Drug-Ibuprofen

HP4-SBE2-β-CD (10 g) was precisely weighed and mixed with the pure water (10 ml), heated, then added with 4 g of ibuprofen, after fully mixed for 3 h under stirring, then filtered, dried under pressure reduction and normal temperature condition, thus white solid inclusion complex is prepared.
1) Determination of Inclusion Constant of Ibuprofen and Hydroxypropyl-Sulfobutyl-β-Cyclodextrin PBS of PH6.86 was used to prepare ibuprofen dilute solution, and this dilute solution was used to prepare HP4-SBE2-β-CD sample solution. Assume that the UV absorption value (A0) of ibuprofen dilute solution under the wavelength of 265 nm was A0, and the sample concentration of HP4-SBE2-β-CD was changed to $1.67 \times 10^{-4} \sim 8.94 \times 10^{-4}$ mol/L, then the UV absorption (A1-An) under different HP4-SBE2-β-CD concentration systems was obtained by the formula $1/\Delta A = 1/(\Delta \epsilon \, K_a \, [G]_0 [CD]_0) + 1/\Delta \epsilon \, [G]_0$. A straight line by $1/\Delta A$ against $1/[CD]_0$ was plotted, and the inclusion constant Ka of ibuprofen/HP4-SBE2-β-CD can be obtained according to the value of intercept/slope.
2) Display Thermal Analysis Validation Test of Inclusion Complex 5.0 mg of ibuprofen, HP4-SBE2-β-CD, physical mixture of ibuprofen and FP4-SBE2-β-CD, and ibuprofen inclusion complex of HP4-SBE2-β-CD samples were weighed respectively, and display thermal analysis by scanning was conducted: reference: Al2O3, range: ±50 μV, temperature rise range: 40° C. 400° C., rate of heat rise: 10° C./min, and the DTA spectrum was thus obtained.
3) Solubilizing Test of Ibuprofen Appropriate amount of ibuprofen was precisely weighed, dissolved with pH6.86 phosphate buffer solution and adjusted to the constant volume, then diluted to different multiples, then measure the UV absorptivity A under 265 nm. The standard curve was plotted by A against concentration C (μg/mL) to obtain C=22.53A−0.2696, R2=0.9998. Different degrees of substitution of hydroxypropyl-sulfobutyl-β-CD: HP2-SBE3-β-CD, HP3-SBE6-β-CD, HP6-SBE2-β-CD, were prepared to the solutions of concentration 10%, then added with excessive amount of ibuprofen, oscillated for 12 h at 25° C.±1° C., filtered, and then fetched appropriate amount of filtrate, diluted by buffer solution, then the photoabsorption intensity was measured at 265 nm, then the solubilization multiples of different samples for the ibuprofen were obtained.

EXAMPLE 14

Inclusion of Hydroxypropyl-Sulfobutyl-β-Cyclodextrin and Non-Ionic Drug-Puerarin 9 g of HP4-SBE2-β-CD was precisely weighed and mixed with the 10 ml of pure water, then added with 1.83 g of puerarin, after fully mixed for 0.5 h under stirring, cooled down at 5° C.; then filtered, dried under pressure reduction and normal temperature condition, thus white solid inclusion complex is prepared.

1) Determination of Inclusion Constant of Puerarin and Hydroxypropyl-Sulfobutyl-β-Cyclodextrin PBS of PH6.86 was used to prepare puerarin dilute solution, and this dilute solution was used to prepare HP4-SBE2-β-CD sample solution. Assume that the UV absorption value (A0) of puerarin dilute solution under the wavelength of 250 nm was A0, and the sample concentration of HP4-SBE2-β-CD was changed to 1.67×10−4~8.94×10−4 mol/L, then the UV absorption (A1-An) of different HP4-SBE2-β-CD concentration groups was obtained by the formula 1/ΔA=1/(As Ka [G]0[CD]0)+1/Δε [G]0. A straight line by 1/ΔA against 1/[CD]0 was plotted, and the inclusion constant Ka of puerarin/HP4-SBE2-β-CD can be obtained according to the value of intercept/slope.

2) Display Thermal Analysis Validation Test of Inclusion Complex 5.0 mg of puerarin, HP4-SBE2-β-CD, physical mixture of puerarin and HP4-SBE2-β-CD, and puerarin inclusion complex of HP4-SBE2-β-CD samples were weighed respectively, and display thermal analysis by scanning was conducted: reference: Al2O3, range: ±50 μV, temperature rise range: 40° C.~400° C., rate of heat rise: 10° C./min, and the DTA spectrum was thus obtained.

3) Solubilizing Test of Puerarin

Appropriate amount of puerarin was precisely weighed, dissolved with pH6.86 phosphate buffer solution and adjusted to the constant volume, then diluted to different multiples, then measure the UV absorptivity A under 250 nm. The standard curve was plotted by concentration C against A (μg/mL) to obtain A=66.608 C+0.0017 R2=0.9999. Different degrees of substitution of hydroxypropyl-sulfobutyl-β-CD: HP2-SBE3-β-CD, HP3-SBE6-β-CD, HP6-SBE2-β-CD, were prepared to the solutions of concentration 10%, then added with excessive amount of puerarin, oscillated for 12 h at 25° C.±1° C., filtered, and then fetched of appropriate amount of filtrate, diluted by buffer solution, then the photoabsorption intensity was measured at 250 nm, then the solubilization multiples of different degrees of substitution of samples for puerarin were obtained.

EXAMPLE 15

Hemolytic Test of Hydroxypropyl-Sulfobutyl-β-Cyclodextrin Drug Carrier 10 ml of fresh rabbit blood were fetched to a clean conical flask, stirred with glass rod for 10 min to remove the fibers, then added with about 20 times of normal saline solution and placed in the centrifuge, 1500 rps/min, for about 3 min, then the supernatant was removed, washed repeated for several times until the supernatant solution becomes clear. The prepared red blood cells were prepared to 5% of suspension by normal saline solution. (Reference: State Drug Administration, Technical requirement of TCM injection study, Technical requirement of TCM new drug study, 1999, 11, 12)

Taking 11 kinds of compounds herein for examples, with the exception of medicinal-β-CD which has poor solubility and can be only prepared into an initial concentration of 13 mmol; 11 kinds of compounds, medicinal—hydroxypropyl-β-CD, SBE6.1-β-CD, SBE4-β-CD were (sulfobutyl-β-cyclodextrin series of samples were obtained from the new drug research center of Nanjing Normal University and the preparation reference: QI QU, EDWARD TUCKER and SHERRIL D. CHRISTIAN: Sulfoalkyl Ether β-Cyclodextrin Derivatives: Synthesis and Characterizations. Journal of Inclusion Phenomena and Macrocyclic Chemistry 43: 213-221, 2002.) prepared into isoosmotic solutions of initial concentration of 40 mmol according to the method shown in the table below, then shaken for 30 min at 37° C., cooled down, centrifuged at 2500 rps/min for about 5 min, then the supernatant was taken to measure the UV absorptivity at =543 nm, the percentage of hemolysis is calculated according to the following formula:

Hemolysis percentage=(A testee−A negative control)/A positive control×100%

TABLE 10

Preparation of the solutions for hemolytic test

| | Tube # | | | | | | |
|---|---|---|---|---|---|---|---|
| | 1 | 2 | 3 | 4 | 5 | 6 | 7 |
| 5% erythrocyte (ml) | 0.5 | 0.5 | 0.5 | 0.5 | 0.5 | 0.5 | 0.5 |
| Normal Saline Solution (ml) | | 1.0 | 2.3 | 2.9 | 3.4 | 3.5 | |
| Distilled water (ml) | | | | | | | 3.5 |
| Testee (ml) | 3.5 | 2.5 | 1.2 | 0.6 | 0.1 | | |
| Concentration of testee (mmol) | 35 | 25 | 12 | 6 | 1 | | |

EXAMPLE 16

Acute toxicity test of hydroxypropyl-sulfobutyl-β-cyclodextrin (Bibliography: State Drug Administration Bureau: "Technical Requirements of Traditional Chinese New Drug Rearch" 12 Nov. 1999)

Preparation method and storage conditions: 7 g of HP4-SBE3-β-CD was precisely weighed to prepare into HP4-SBE3-β-CD suspension solution, and tested drugs were prepared prior clinical application. Tested drugs must be kept at room temperature.

Animal: Kunming mice were provided by Institute of Medicine Laboratory Animal Center, Southeast University. The mice were about 40 days and their average weight is 20±2 g, half-male and half-female.

Setting of test group and drug dosage: 20 mice for each group, one dosage group.

Administration method and approach: intragastric administration and intravenous injection. A single administration was conducted to animals. Due to concentration limit of tested substance, the animals can not be administrated according to $LD_{50}$ test, therefore the maximum administration test was carried out. The maximum amount of intragastric administration was subject to 40 ml/kg per day. Intravenous injection amount is 25 ml/kg, after administration, the toxicity reaction situation, weight changes and animal deaths of the test animals were observed and recorded.

Test conditions: laboratory temperature: 18~25° C., humidity: 40-60%, 12-hour light and 12-h dark alternatively. Five mice with the same gender were fed in the same cage of the size 18×29×16 cm and the feed is full granuled feed, drinking water freely. Wood shaving sawdust was used for padding materials, which was replaced 1-2 times every week.

Indicators observed: The toxicity reaction and the number of animals killed in each group were observed on the 14th day after drug administration. If necessary, gross anatomy is to be conducted to observe the visceral pathological changes. Animal body weights of each group were weighed after finishing the test.

EXAMPLE 17

General pharmacological test of hydroxypropyl-sulfobutyl-β-cyclodextrin—effect on mouse' neural and mental system (Bibliography: 1. Xu, Shuyun, Pharmacological Experimental Methodology, 2nd version, P. 641, People Health Press, Beijing, 1991. 2. Department of Medical Administration, the Ministry of Health: Guidelines on Preclinical Study of New Pharmaceuticals (weaten drags), P. 42, July, 1993.)

Preparation methods and storage conditions: The HP4-SBE3-β-CD was kept in dark refrigerator. Prepare into the required concentration with normal saline solution prior to use.

Animals and feeding conditions: Kunming mice, 18~22 g, half male and half female, provided by Laboratory Animal Center, Southeast University; the animal environmental facility qualification number: 97004; the quality certification number of the experimental animals: No. 97006. The mice were fed for three day in the laboratory prior to use.

Feeding conditions: The mice tested were fed with cage and the plastic cage size: 32×18×18 cm; each cage had 5 mice of the same gender. The basic feed is full nutrient granuled feed, prepared by the Experimental Center, drinking water freely. The laboratory temperature: 22-26° C., and the relative humidity: 40-60%, with ventilation condition.

Apparatus: 6-light channel SYS-I mouse spontaneous activity detector, self-made.

Positive control drug: Chlorpromazine Hydrochloride Injection, 50 mg/2 ml, Batch No.: 20040509, produced by Beijing Yongkang Pharmaceutical Factory; Dizepam Injection, 10 mg/2 ml, Batch No.: 041101, Produced of Shanghai Xudong Haipu Pharmaceutical Co., Ltd.

Effect on mice's ordinary behaviors: 40 mice were randomly divide into four groups, control group, administration dose groups of 80 mg/kg, 160 mg/kg and 320 mg/kg respectively; one-time intragastric administration, the mice of the control group were given the constant volume of normal saline solution (blank), then were administer of drugs, after 0.5 hour, 1 hour, 2 hours and 3 hours, observed the ordinary behaviors of the mice for one time, recorded the crawal, pilo-erection, slow breathing, polysialia, vibration, screaming, jumping, vertical tail, attack & biting, sound and tactile stimulation response, gait, righting reflex, earlap and caudal blood vessel color, body temperature, eye crack size, pupil changes, etc, and recorded the abnormality and compared with the control groups.

Effect on the frequency of mice' spontaneous activities: healthy mice, and 50 mice whose frequency of activities was 220-320 within 5 min were selected and randomly divided into five groups, the establishment of dosages were the same as the above. The frequency of activity at o min were measured before drug administration, and then were conducted by intragastric administration, 30, 60, 120 and 180 min later, the frequency of activities within 5 min was measured and recorded respectively, then compared with that of the control group. The measuring time was the period between 9:00 am and 4:00 pm each day. A Six-light channel spontaneous activity instrument was used for one mouse, kept at 24-26° C. of room temperature of; and kept quiet; the test was carried out after the test boxes were covered with black cloth. The test results were shown in Table 13.

Effect on balance movement (Balane test): 50 mice, half male and half female were randomly divided into five groups, the dosage setting and administration method were the same as the above. The mice were firstly selected before drug application, and those qualified would be used for test. When testing, the mice were placed on a wooden bar with diameter of 0.8 cm, length of 60 cm and 60 cm from the ground. And if the mouse would not fall within 3 min, it is qualified, then administrated with drugs. Repeated the test at 30, 60, 120 and 180 min after administration of drugs, and if the mouse fell over three times, it meant balance loss and the falling rate was calculated thereof. The difference between the administration group and control group were compared.

EXAMPLE 18

General pharmacological test of hydroxypropyl-sulfobutyl-β-cyclodextrin—effect on respiratory and cardiovascular system of the anesthetic dogs (Bibliography: Department of Medical Administration, the Ministry of Health: Guidelines on Preclinical Study of New Pharmaceuticals (weaten drugs), P. 42, July, 1993)

Preparation method: Normal saline solution was used to prepare into the concentration level required.

Test animals: The animal tested was Beagle dog, provided by Zhongke Xishan Laboratory Animals Co., Ltd. The animal's qualified number: Zhongke Hu Animal Management No. 99-0011. The Facility Environment qualified number: Zhongke Hu Animal Management Number: No. 99-0010. Prior to test, they were weighed and their food intake was observed, and their ordinary behaviours were observed.

Experimental instruments: RM-6000 polygraph (Japan photoelectricity); WDT-204 automatic balance recording meter (made in Shanghai Dahua Instrument and Meter Plant).

Specific experimental method: 24 domestic dogs were randomly divided into four groups and each group had six dogs. After intraperitoneal injection of sodium pentobarbital of 40 mg/kg and anesthesia (sodium pentobarbital 4 mg/kg was added through intravenous injection after each 1 h), right carotid artery was separated by back fixed and TP-101 pressure transducer was connected through intubation and a polygraph was used to record the contraction pressure (SAP), diastolic blood pressure (DAP) and mean arterial pressure (MAP); Needle-shaped electrode was pierced into limb subcutaneous and 11 lead electrocardiogram (ECG) was recorded, then the trachea was separated and cut open, the endrotracheal intubation connection respiratory transducer was inserted to scan and record the respiratory frequency and magnitude. Left femoral vein was separated and the venous intubation was used to add sodium pentobarbital. Median abdominal incision was conducted to identify the duodenum for administration. 40, 80 and 160 mg/kg three-dose groups were established and the control group was the constant volume of normal saline solution. The above various indicators were recorded as pre-drug value about 20 minutes after operation, and then the duodenum was injected into different doses of HP4-SBE3-β-CD with injection time of 30 seconds and a volume of 1.0 ml/kg, and then the above indicators were respectively recorded at the time of 5, 10, 30, 60, 120 and 180 min prior to administration and after administration, and the effects of the tested drug HP4-SBE3-β-CD on respiratory frequency, magnitude and electrocardio and blood pressure were observed. Data of the tests before and after drug administration should be processed by t-test.

EXAMPLE 19 the procedure was carried out basically the same as Example 1, but, wherein, 0.08 mol of sodium hydroxide, 0.04 mol of 1,4-butyl sultone and 0.055 mol of 1,2-propylene oxide were added respectively, thus HP2-SBE1-β-CD product was prepared, with the production rate of 100.43%.

EXAMPLE 20 the procedure was carried out basically the same as Example 1, but, wherein, 0.08 mol of sodium hydroxide, 0.04 mol of 1,4-butyl sultone and 0.08 mol of 1,2-propylene oxide were added respectively, thus HP3-SBE1-β-CD product was prepared, with the production rate of 99.57%.

EXAMPLE 21 the procedure was carried out basically the same as Example 1, but, wherein, 0.08 mol of sodium hydroxide, 0.04 mol of 1,4-butyl sultone and 0.11 mol of 1,2-propylene oxide were added respectively, thus HP4-SBE1-β-CD product was prepared, with the production rate of 103.03%.

EXAMPLE 22 the procedure was carried out basically the same as Example 1, but, wherein, 0.08 mol of sodium hydroxide, 0.04 mol of 1,4-butyl sultone and 0.014 mol of 1,2-propylene oxide were added respectively, thus HP5-SBE1-β-CD product was prepared, with the production rate of 109.36%.

EXAMPLE 23 the procedure was carried out basically the same as Example 1, but, wherein, 0.08 mol of sodium hydroxide, 0.04 mol of 1,4-butyl sultone and 0.017 mol of 1,2-propylene oxide were added respectively, thus HP6-SBE1-β-CD product was prepared, with the production rate of 107.24%.

EXAMPLE 24 the procedure was carried out basically the same as Example 1, but, wherein, 0.08 mol of sodium hydroxide, 0.04 mol of 1,4-butyl sultone and 0.020 mol of 1,2-propylene oxide were added respectively, thus HP7-SBE1-β-CD product was prepared, with the production rate of 112.02%.

EXAMPLE 25 the procedure was carried out basically the same as Example 1, but, wherein, 0.08 mol of sodium hydroxide, 0.05 mol of 1,4-butyl sultone and 0.03 mol of 1,2-propylene oxide were added respectively, thus HP1-SBE2-β-CD product was prepared, with the production rate of 109.89%.

EXAMPLE 26 the procedure was carried out basically the same as Example 1, but, wherein, 0.08 mol of sodium hydroxide, 0.05 mol of 1,4-butyl sultone and 0.05 mol of 1,2-propylene oxide were added respectively, thus HP2-SBE2-β-CD product was prepared, with the production rate of 1.16%.

EXAMPLE 27 the procedure was carried out basically the same as Example 1, but, wherein, 0.08 mol of sodium hydroxide, 0.05 mol of 1,4-butyl sultone and 0.07 mol of 1,2-propylene oxide were added respectively, thus HP3-SBE2-β-CD product was prepared, with the production rate of 113.52%.

EXAMPLE 28 the procedure was carried out basically the same as Example 1, but, wherein, 0.08 mol of sodium hydroxide, 0.05 mol of 1,4-butyl sultone and 0.10 mol of 1,2-propylene oxide were added respectively, thus HP4-SBE2-β-CD product was prepared, with the production rate of 113.58%.

EXAMPLE 29 the procedure was carried out basically the same as Example 1, but, wherein, 0.08 mol of sodium hydroxide, 0.05 mol of 1,4-butyl sultone and 0.14 mol of 1,2-propylene oxide were added respectively, thus HP5-SBE2-β-CD product was prepared, with the production rate of 109.89%.

EXAMPLE 30 the procedure was carried out basically the same as Example 1, but, wherein, 0.08 mol of sodium hydroxide, 0.05 mol of 1,4-butyl sultone and 0.17 mol of 1,2-propylene oxide were added respectively, thus HP6-SBE2-β-CD product was prepared, with the production rate of 111.93%.

EXAMPLE 31 the procedure was carried out basically the same as Example 1, but, wherein, 0.08 mol of sodium hydroxide, 0.05 mol of 1,4-butyl sultone and 0.20 mol of 1,2-propylene oxide were added respectively, thus HP7-SBE2-β-CD product was prepared, with the production rate of 116.43%.

EXAMPLE 32 the procedure was carried out basically the same as Example 1, but, wherein, 0.08 mol of sodium hydroxide, 0.05 mol of 1,4-butyl sultone and 0.23 mol of 1,2-propylene oxide were added respectively, thus HP8-SBE2-β-CD product was prepared, with the production rate of 118.21%.

EXAMPLE 33 the procedure was carried out basically the same as Example 1, but, wherein, 0.11 mol of sodium hydroxide, 0.08 mol of 1,4-butyl sultone and 0.03 mol of 1,2-propylene oxide were added respectively, thus HP1-SBE3-β-CD product was prepared, with the production rate of 107.55%.

EXAMPLE 34 the procedure was carried out basically the same as Example 1, but, wherein, 0.11 mol of sodium hydroxide, 0.08 mol of 1,4-butyl sultone and 0.12 mol of 1,2-propylene oxide were added respectively, thus HP3-SBE3-β-CD product was prepared, with the production rate of 111.75%.

EXAMPLE 35 the procedure was carried out basically the same as Example 1, but, wherein, 0.11 mol of sodium hydroxide, 0.08 mol of 1,4-butyl sultone and 0.15 mol of 1,2-propylene oxide were added respectively, thus HP4-SBE3-β-CD product was prepared, with the production rate of 107.55%.

EXAMPLE 36 the procedure was carried out basically the same as Example 1, but, wherein, 0.11 mol of sodium hydroxide, 0.08 mol of 1,4-butyl sultone and 0.16 mol of 1,2-propylene oxide were added respectively, thus HP5-SBE3-β-CD product was prepared, with the production rate of 109.02%.

EXAMPLE 37 the procedure was carried out basically the same as Example 1, but, wherein, 0.11 mol of sodium hydroxide, 0.08 mol of 1,4-butyl sultone and 0.20 mol of 1,2-propylene oxide were added respectively, thus HP6-SBE3-β-CD product was prepared, with the production rate of 111.15%.

EXAMPLE 38 the procedure was carried out basically the same as Example 1, but, wherein, 0.11 mol of sodium hydroxide, 0.08 mol of 1,4-butyl sultone and 0.23 mol of 1,2-propylene oxide were added respectively, thus HP7-SBE3-β-CD product was prepared, with the production rate of 111.07%.

EXAMPLE 39 the procedure was carried out basically the same as Example 2, but, wherein, 0.15 mol of sodium hydroxide, 0.12 mol of 1,4-butyl sultone and 0.04 mol of 1,2-propylene oxide were added respectively, thus HP1-SBE4-β-CD product was prepared, with the production rate of 106.33%.

EXAMPLE 40 the procedure was carried out basically the same as Example 1, but, wherein, 0.15 mol of sodium hydroxide, 0.12 mol of 1,4-butyl sultone and 0.06 mol of 1,2-propylene oxide were added respectively, thus HP2-SBE4-β-CD product was prepared, with the production rate of 103.16%.

EXAMPLE 41 the procedure was carried out basically the same as Example 40, but, wherein, 0.15 mol of sodium hydroxide, 0.12 mol of 1,4-butyl sultone and 0.09 mol of 1,2-propylene oxide were added respectively, thus HP4-SBE4-β-CD product was prepared, with the production rate of 105.11%.

EXAMPLE 42 the procedure was carried out basically the same as Example 40, but, wherein, 0.15 mol of sodium hydroxide, 0.12 mol of 1,4-butyl sultone and 0.12 mol of 1,2-propylene oxide were added respectively, thus HP5-SBE4-β-CD product was prepared, with the production rate of 108.45%.

EXAMPLE 43 the procedure was carried out basically the same as Example 40, but, wherein, 0.15 mol of sodium hydroxide, 0.12 mol of 1,4-butyl sultone and 0.16 mol of 1,2-propylene oxide were added respectively, thus HP6-SBE4-β-CD product was prepared, with the production rate of 111.18%.

EXAMPLE 44 the procedure was carried out basically the same as Example 40, but, wherein, 0.18 mol of sodium hydroxide, 0.15 mol of 1,4-butyl sultone and 0.055 mol of 1,2-propylene oxide were added respectively, thus HP1-SBE5-β-CD product was prepared, with the production rate of 109.34%.

EXAMPLE 45 the procedure was carried out basically the same as Example 40, but, wherein, 0.18 mol of sodium hydroxide, 0.15 mol of 1,4-butyl sultone and 0.08 mol of 1,2-propylene oxide were added respectively, thus HP2-SBE5-β-CD product was prepared, with the production rate of 110.70%.

EXAMPLE 46 the procedure was carried out basically the same as Example 40, but, wherein, 0.18 mol of sodium hydroxide, 0.15 mol of 1,4-butyl sultone and 0.095 mol of 1,2-propylene oxide were added respectively, thus HP3-SBE5-β-CD product was prepared, with the production rate of 112.45%.

EXAMPLE 47 the procedure was carried out basically the same as Example 40, but, wherein, 0.18 mol of sodium hydroxide, 0.15 mol of 1,4-butyl sultone and 0.13 mol of 1,2-propylene oxide were added respectively, thus HP4-SBE5-β-CD product was prepared, with the production rate of 111.86%.

EXAMPLE 48 the procedure was carried out basically the same as Example 40, but, wherein, 0.18 mol of sodium hydroxide, 0.15 mol of 1,4-butyl sultone and 0.17 mol of 1,2-propylene oxide were added respectively, thus HP5-SBE5-β-CD product was prepared, with the production rate of 116.06%.

EXAMPLE 49 the procedure was carried out basically the same as Example 3, but, wherein, 0.20 mol of sodium hydroxide, 0.16 mol of 1,4-butyl sultone and 0.08 mol of 1,2-propylene oxide were added respectively, thus HP1-SBE6-β-CD product was prepared, with the production rate of 117.57%.

EXAMPLE 50 the procedure was carried out basically the same as Example 3, but, wherein, 0.20 mol of sodium hydroxide, 0.16 mol of 1,4-butyl sultone and 0.13 mol of 1,2-propylene oxide were added respectively, thus HP2-SBE6-βCD product was prepared, with the production rate of 115.66%.

EXAMPLE 51 the procedure was carried out basically the same as Example 3, but, wherein, 0.20 mol of sodium hydroxide, 0.16 mol of 1,4-butyl sultone and 0.16 mol of 1,2-propylene oxide were added respectively, thus HP4-SBE6-β-CD product was prepared, with the production rate of 114.82%.

EXAMPLE 52 the procedure was carried out basically the same as Example 2, but, wherein, 0.21 (0.02+0.19) mol of sodium hydroxide, 0.19 mol of 1,4-butyl sultone and 0.03 mol of 1,2-propylene oxide were added respectively, thus HP1-SBE7-β-CD product was prepared, with the production rate of 116.11%.

EXAMPLE 53 the procedure was carried out basically the same as Example 40, but, wherein, 0.21 mol of sodium hydroxide, 0.19 mol of 1,4-butyl sultone and 0.06 mol of 1,2-propylene oxide were added respectively, thus HP2-SBE7-β-CD product was prepared, with the production rate of 117.23%.

EXAMPLE 54 the procedure was carried out basically the same as Example 40, but, wherein, 0.21 mol of sodium hydroxide, 0.19 mol of 1,4-butyl sultone and 0.09 mol of 1,2-propylene oxide were added respectively, thus HP3-SBE7-β-CD product was prepared, with the production rate of 113.17%.

EXAMPLE 55 the procedure was carried out basically the same as Example 2, but, wherein, 0.29 (0.02+0.27) mol of sodium hydroxide, 0.27 mol of 1,4-butyl sultone and 0.03 mol of 1,2-propylene oxide were added respectively, thus HP1-SBE8-β-CD product was prepared, with the production rate of 119.67%.

EXAMPLE 56 the procedure was carried out basically the same as Example 40, but, wherein, 0.24 mol of sodium hydroxide, 0.22 mol of 1,4-butyl sultone and 0.06 mol of 1,2-propylene oxide were added respectively, thus HP2-SBE8-β-CD product was prepared, with the production rate of 117.54%.

EXAMPLE 57 the procedure was carried out basically the same as Example 1, but, wherein, 0.08 mol of sodium hydroxide, 0.04 mol of 1,4-butyl sultone and 0.023 mol of 1,2-propylene oxide were added respectively, thus HP8-SBE1-β-CD product was prepared, with the production rate of 118.76%.

What is claimed is:

1. A hydroxypropyl-sulfobutyl-β-cyclodextrin, wherein said hydroxypropyl-sulfobutyl-β-cyclodextrin is a cyclodextrin derivative mixed substituted by hydroxypropyl and sulfobutyl groups: n-(2,3,6-O-2-hydroxypropyl)-m-(2,3,6-O-sulfobutyl)-β-cyclodextrin, wherein said cyclodextrin derivative has the following structure denoted by the following general formula:

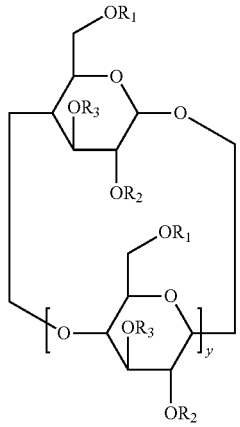

y = 6
$R_1 = H, R_2 = (CH_2)_4SO_3-X, R_3 = CH_2CH(OH)CH_3$, or
$R_1 = H, R_2 = CH_2CH(OH)CH_3, R_3 = (CH_2)_4SO_3-X$, or
$R_1 = (CH_2)_4SO_3-X, R_2 = H, R_3 = CH_2CH(OH)CH_3$, or
$R_1 = CH_2CH(OH)CH_3, R_2 = H, R_3 = (CH_2)_4SO_3-X$, or
$R_1 = (CH_2)_4SO_3-X, R_2 = CH_2CH(OH)CH_3, R_3 = H$, or
$R_1 = CH_2CH(OH)CH_3, R_2 = (CH_2)_4SO_3-X, R_3 = H$, or
$R_1 = R_2 = (CH_2)_4SO_3-X, R_3 = CH_2CH(OH)CH_3, H$, or
$R_1 = R_3 = (CH_2)_4SO_3-X, R_2 = CH_2CH(OH)CH_3, H$, or
$R_2 = R_3 = (CH_2)_4SO_3-X, R_1 = CH_2CH(OH)CH_3, H$, or
$R_1 = R_2 = CH_2CH(OH)CH_3, R_3 = (CH_2)_4SO_3-X, H$, or
$R_1 = R_3 = CH_2CH(OH)CH_3, R_2 = (CH_2)_4SO_3-X, H$, or
$R_2 = R_3 = CH_2CH(OH)CH_3, R_1 = (CH_2)_4SO_3-X, H$, or
$R_1 = R_2 = H, R_3 = CH_2CH(OH)CH_3, (CH_2)_4SO_3-X$, or
$R_1 = R_3 = H, R_2 = CH_2CH(OH)CH_3, (CH_2)_4SO_3-X$, or
$R_2 = R_3 = H, R_1 = CH_2CH(OH)CH_3, (CH_2)_4SO_3-X$
$X = Na, K, Li$.

2. The hydroxypropyl-sulfobutyl-β-cyclodextrin of claim 1, wherein the number of substituent groups per mole cyclodextrin is n hydroxypropyl groups and m sulfobutyl groups; "n" represents the average degree of substitution of hydroxypropyl groups; "m" represents the average degree of substitution of sulfobutyl groups; "n+m=z" is the gross average degree of substitution, in which n is a random integer selected among 1,2,3,4,5,6,7,8,9; m is a random integer selected among 1,2,3,4,5,6,7,8,9; and the gross average degree of substitution z is a random integer selected among 2,3,4,5,6,7,8,9,10.

3. The hydroxypropyl-sulfobutyl-β-cyclodextrin of claim 2, wherein said hydroxypropyl-sulfobutyl-β-cyclodextrin is selected among:

| | |
|---|---|
| $HP_2$-$SBE_3$-β-CD; Z = 5, | $HP_1$-$SBE_4$-β-CD; Z = 5, |
| $HP_3$-$SBE_6$-β-CD; Z = 9, | $HP_2$-$SBE_2$-β-CD; Z = 4, |
| $HP_3$-$SBE_2$-β-CD; Z = 5, | $HP_3$-$SBE_4$-β-CD; Z = 7, |
| $HP_4$-$SBE_2$-β-CD; Z = 6, | $HP_4$-$SBE_3$-β-CD; Z = 7, |
| $HP_5$-$SBE_2$-β-CD; Z = 7, | $HP_5$-$SBE_3$-β-CD; Z = 8, |
| $HP_6$-$SBE_2$-β-CD; Z = 8. | |

4. The hydroxypropyl-sulfobutyl-β-cyclodextrin of claim 1 or claim 2 or claim 3, wherein said hydroxypropyl-sulfobutyl-β-cyclodextrin is cyclodextrin derivative of X=Na, K, Li.

5. The hydroxypropyl-sulfobutyl-β-cyclodextrin as claimed in claim 4, wherein said cyclodextrin derivative of X=Na, K, Li is selected among:

| | | |
|---|---|---|
| $HP_2$-$SBE_3$-β-CD | $HP_3$-$SBE_4$-β-CD | $HP_5$-$SBE_3$-β-CD |
| $HP_1$-$SBE_4$-β-CD | $HP_4$-$SBE_2$-β-CD | $HP_6$-$SBE_2$-β-CD |
| $HP_3$-$SBE_6$-β-CD | $HP_4$-$SBE_3$-β-CD | $HP_3$-$SBE_2$-β-CD |
| $HP_2$-$SBE_2$-β-CD | $HP_5$-$SBE_2$-β-CD | |

6. The hydroxypropyl-sulfobutyl-β-cyclodextrin of claim 5, wherein said average degree of substitution of n and m also includes the actual average value ±0.5, the range of average degree of substitution is:

| | |
|---|---|
| $HP_2$-$SBE_3$-β-CD | n = 1.5~2.4; m = 2.5~3.4 |
| $HP_1$-$SBE_4$-β-CD | n = 1.0~1.4; m = 3.5~4.4 |
| $HP_3$-$SBE_6$-β-CD | n = 2.5~3.4; m = 5.5~6.4 |
| $HP_2$-$SBE_2$-β-CD | n = 1.5~2.4; m = 1.5~2.4 |
| $HP_3$-$SBE_4$-β-CD | n = 2.5~3.4; m = 3.5~4.4 |
| $HP_4$-$SBE_2$-β-CD | n = 3.5~4.4; m = 1.5~2.4 |
| $HP_4$-$SBE_3$-β-CD | n = 3.5~4.4; m = 2.5~3.4 |
| $HP_5$-$SBE_2$-β-CD | n = 4.5~5.4; m = 1.5~2.4 |

-continued

| | |
|---|---|
| $HP_5\text{-}SBE_3\text{-}\beta\text{-}CD$ | n = 4.5~5.4; m = 2.5~3.4 |
| $HP_6\text{-}SBE_2\text{-}\beta\text{-}CD$ | n = 5.5~6.4; m = 1.5~2.4 |
| $HP_3\text{-}SBE_2\text{-}\beta\text{-}CD$ | n = 2.5~3.4; m = 1.5~2.4 |

7. The hydroxypropyl-sulfobutyl-β-cyclodextrin of claim 5 or claim 6, wherein the content of unmodified cyclodextrin is not more than 1.5%.

8. The preparation method of said hydroxypropyl-sulfobutyl-β-cyclodextrin of claim 1, the method comprising:
   combining 2-4 times of water by weight and 2-17 molar equivalents of base to cyclodextrin;
   slowly adding a first and second reagent selected from 2-15 molar equivalents of 1,4-butyl sultone and 1.5-13 molar equivalents of 1,2-propylene oxide to the cyclodextrin solution, wherein either reagent may be the first reagent, and the first reagent is allowed to react for 5-8 h before addition of the second reagent that reacts for an additional 5-8 h;
   adding a supplemental 2-15 molar equivalents of base after 1,2-propylene oxide has reacted when 1,2-propylene oxide is added first; and
   wherein 1,4-butyl sultone reacts at 80° C., and 1,2-propylene oxide reacts at room temperature to produce a crude product of hydroxypropyl-sulfobutyl-β-cyclodextrin that is neutralized to a pH of 6-7 with hydrochloric acid, and filtered, further wherein the filtrate is dialyzed and dried under the condensation and pressure reduction condition to obtain the product.

9. The preparation method of said hydroxypropyl-sulfobutyl-β-cyclodextrin of claim 8, wherein the specific steps can be one of the following two options:
   the cyclodextrin is added with 2-4 times of water by weight and 2 molar equivalents of base, stirred at room temperature then reacted with 1.5-13 molar equivalents of 1,2-propylene oxide, and reacted for 7-8 hours, then 2-15 molar equivalents of base is added, heated to 80° C., then reacted with 2-15 molar equivalents of 1,4-butyl sultone for 5-8 hours, to produce hydroxypropyl-sulfobutyl-β-cyclodextrin product of specific degree of substitution;
   or the cyclodextrin is added with 2-4 times of water by weight and 3-17 molar equivalents of base, stirred and heated to 80° C., then reacted with 2-15 molar equivalents of 1,4-butyl sultone for 5-8 hours, cooled down to room temperature, then under the controlled room temperature, reacted with 1.5-13 molar equivalents of 1,2-propylene oxide for 7-8 hours, to produce hydroxypropyl -sulfobutyl-β-cyclodextrin product of specific degree of substitution.

10. The preparation method of said hydroxypropyl-sulfobutyl-β-cyclodextrin of claim 8, wherein unmodified cyclodextrin is used as raw material, and mixed substitution of continuous feeding reaction steps without separation of reaction intermediate is adopted.

11. The analytic method of said hydroxypropyl-sulfobutyl-β-cyclodextrin of claim 1, wherein hydroxypropyl-sulfobutyl-β-cyclodextrin product is dissolved by water, or methanol, or ethanol, or acetonitrile, or methanol-water, or ethanol-water, or acetonitrile-water solution, or two or three of solutions thereof, the product is analyzed by chromatography with sample solution.

12. The analytic method of said hydroxypropyl-sulfobutyl-β-cyclodextrin of claim 11, wherein said analytic method is to analyze the product content or purity by High-Performance Liquid Chromatography.

13. The analytic method of said hydroxypropyl-sulfobutyl-β-cyclodextrin of claim 11, wherein said analytic method is to analyze the organic impurities of the product by gas chromatography.

14. The hydroxypropyl-sulfobutyl-β-cyclodextrin of claim 1, wherein said hydroxypropyl-sulfobutyl-β-cyclodextrin is used for preparation of combination for medical purpose by inclusion or mixture with active molecule as excipients.

15. The pharmaceutical application of hydroxypropyl-sulfobutyl-β-cyclodextrin of claim 14, wherein said hydroxypropyl-sulfobutyl-β-cyclodextrin combination is used as oral preparations for treatment or health care purpose.

16. The pharmaceutical application of hydroxypropyl-sulfobutyl-β-cyclodextrin of claim 14, wherein said hydroxypropyl-sulfobutyl-β-cyclodextrin combination is used as non-oral preparations for treatment or health care purpose.

* * * * *